United States Patent [19]

Billig et al.

[11] Patent Number: 4,748,261

[45] Date of Patent: May 31, 1988

[54] BIS-PHOSPHITE COMPOUNDS

[75] Inventors: Ernst Billig; Anthony G. Abatjoglou, both of Charleston; David R. Bryant, South Charleston, all of W. Va.

[73] Assignee: Union Carbide Corporation, Danbury, Conn.

[21] Appl. No.: 772,891

[22] Filed: Sep. 5, 1985

[51] Int. Cl.$^4$ .................. C07F 9/02; C07F 9/141
[52] U.S. Cl. .................. 556/404; 558/85; 556/136; 556/138; 568/451
[58] Field of Search .................. 558/85; 556/404

[56] References Cited

U.S. PATENT DOCUMENTS

| | | | |
|---|---|---|---|
| 3,527,809 | 9/1970 | Pruett et al. | 260/604 |
| 3,655,832 | 4/1972 | Kauder et al. | 260/930 |
| 4,094,855 | 6/1978 | Spivack | 260/45.8 NT |
| 4,143,028 | 3/1979 | Spivack | 260/45.94 D |
| 4,148,830 | 4/1979 | Pruett et al. | 260/604 HF |
| 4,196,117 | 4/1980 | Spivack | 558/85 |
| 4,247,486 | 1/1981 | Brewester et al. | 568/454 |
| 4,252,750 | 2/1981 | Buysch et al. | 260/927 R |
| 4,288,391 | 9/1981 | Spivack | 260/927 R |
| 4,318,845 | 3/1982 | Spivack et al. | 524/91 |
| 4,351,759 | 9/1982 | Spivack | 524/100 |
| 4,362,830 | 12/1982 | Minagawa et al. | 524/101 |
| 4,374,219 | 2/1983 | Spivack | 524/91 |
| 4,400,548 | 8/1983 | Abatjoglou et al. | 568/454 |
| 4,482,749 | 11/1984 | Dennis et al. | 568/454 |
| 4,491,675 | 1/1985 | Abatjoglou et al. | 568/454 |
| 4,496,768 | 1/1985 | Dennis et al. | 568/454 |
| 4,522,933 | 6/1985 | Abatjoglou et al. | 502/161 |
| 4,593,011 | 6/1986 | Abatjoglou et al. | 502/161 |
| 4,599,206 | 7/1986 | Billig et al. | 558/85 |

FOREIGN PATENT DOCUMENTS

| | | |
|---|---|---|
| 96986 | 5/1983 | European Pat. Off. |
| 96988 | 6/1983 | European Pat. Off. |
| 149894 | 7/1985 | European Pat. Off. |

OTHER PUBLICATIONS

"Chem. Ber.", vol. 89, pp. 1119–1123 (1956).
"Chem. Abs.", vol. 51, p. 2661 (1957).
1st page and Search Report of WO85/03702.

*Primary Examiner*—Anton H. Sutto
*Attorney, Agent, or Firm*—Reynold J. Finnegan

[57] ABSTRACT

Transition metal-bis-phosphite catalyzed carbonylation processes, especially hydroformylation, as well as transition metal-bis-phosphite compositions, bis-phosphite ligands and transition metal-bis-phosphite catalysts.

4 Claims, No Drawings

BIS-PHOSPHITE COMPOUNDS

BRIEF SUMMARY OF THE INVENTION

1. Technical Field

This invention relates to novel bis-phosphite ligands and their use in transition metal complex catalyzed reactions. More particularly this invention relates to novel bis-phosphite ligands having both a diorgranophosphite functionality and a triorganophosphite functionality and their use in a transition metal-bis-phosphite complex catalyzed carbonylation process, especially hydroformulation, as well as to transition metal-bis-phosphite ligand complex compositions.

2. Background Art

It is well known in the art that carbonylation reactions are enhanced by the use of a modified Group VIII metal catalysts e.g., catalysts comprising a Group VIII transition metal-phosphorus ligand complex.

Carbonylation processes directed to production of oxygenated products in the presence of a catalyst in general involve the reaction of an organic compound with carbon monoxide and preferably another reactant, especially hydrogen, and are well known in the art, e.g., see J. Falbe, "New Synthesis With Carbon Monoxide" Springer Verlag, New York 1980. Such processes may include the carbonylation of organic compounds such as olefins, acetylenes, alcohols and activated chlorides with carbon monoxide along or with carbon monoxide and either hydrogen, alcohol, amine or water, as well as ring closure reactions of functionally by unsaturated compounds e.g. unsaturated amides with CO. One of the major types of known carbonylation reactions is the hydroformylation of an olefinic compound with carbon monoxide and hydrogen to produce oxygenated products such as aldehydes using a Group VIII transition metal-phosphorus ligand complex, followed by a subsequent aldolization reaction if desired.

However, the search for a more effective phosphorus ligand which will provide a more active or more stable or more all purpose type metal-phosphorus ligand complex catalyst is a constant one in the art and heretofore, unlike the present invention, has been centered for the most part on the use of triorganophosphine, triorganophosphite and diorganophosphite ligands, such as disclosed e.g. in U.S. Pat. No. 3,527,809 and U.S. application Ser. No. 685,025 filed Dec. 28, 1984, now U.S. Pat. No. 4,599,206, issued July 8, 1986.

DISCLOSURE OF INVENTION

It has now been discovered that bis-phosphite ligands of this invention may be employed as the phosphorus ligand in Group VIII transition metal complex catalyzed carbonylation processes to provide numerous advantages relative to heretofore commonly proposed Group VIII transition metal-phosphorus ligand complex catalysts.

For instance, the bis-phosphite ligands employable herein may be useful in providing unique chelated metal complexes having good catalytic activity and stability in carbonylation processes and particularly hydroformylation. Further, the use of the bis-phosphite ligands employable herein provide an excellent means for controlling product selectivity in hydroformylation reactions. For instance, the bis-phosphites have been found to be very effective ligands when oxygenated products, e.g. aldehydes, having very high normal to iso (branched) product ratios are desired. Indeed, the bis-phosphite ligands employable herein, in addition to having been found to provide high n/i aldehyde product ratios from sterically unhindered alpha olefins, have also been found to provide high n/i aldehyde product ratios from internal olefins that are unprecedented in the art.

Thus it is an object of this invention to provide a novel class of bis-phosphite ligand compounds. It is a further object of this invention to provide an improved carbonylation process and especially a hydroformylation process, wherein said process is carried out in the presence of a Group VIII transition metal-bis-phosphite ligand complex catalyst. It is also an object of this invention to provide a novel class of Group VIII transition metal-bis-phosphite ligand complexes suitable for use in such carbonylation and hydroformylation processes. Other objects and advantages of this invention will become readily apparent from the following written description and appended claims.

Accordingly, one aspect of this invention can be described as a novel generic class of bis-phosphite ligands having the general formula

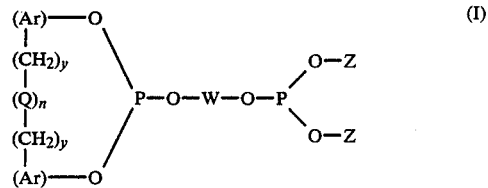

(I)

wherein each Ar group represents an identical or different, substituted or unsubstituted aryl radical; wherein W represents a divalent radical selected from the group consisting of alkylene, arylene and —arylene—(CH$_2$)y—(Q)n—(CH$_2$)y—arylene—, wherein each arylene radical is the same as Ar defined above; wherein each y individually has a value of 0 or 1; wherein each Q individually represents a divalent bridging group selected from the class consisting of —CR$^1$R$^2$—, —O—, —S—, —NR$^3$—, —SiR$^4$R$^5$— and —CO—, wherein each R$^1$ and R$^2$ radical individually represents a radical selected from the group consisting of hydrogen, alkyl of 1 to 12 carbon atoms, phenyl, tolyl and anisyl, wherein each R$^3$, R$_4$, and R$^5$ radical individually represents —H or —CH$_3$; wherein each n individually has a value of 0 or 1; and wherein each Z group individually represents a radical selected from the group consisting of substituted or unsubstituted alkyl, aryl, alkaryl, aralkyl and alicyclic radicals.

Another generic aspect of this invention can be described as a process for carbonylation comprising reacting an organic compound capable of being carbonylated with carbon monoxide (especially a process for hydroformylating olefins to aldehydes) in the presence of a Group VIII transition metal-bis-phosphite ligand complex catalyst wherein the bis-phosphite ligand is a bis-phosphite of Formula (I) above.

Yet another generic aspect of this invention comprises novel Group VIII transition metal-bis-phosphite ligand complexes and catalyst precursor solutions thereof.

DETAILED DESCRIPTION

As seen by the above formula the bis-phosphite ligands employable herein represent an entirely new class of compounds. For example, unlike other phosphite compounds, if hydrolyzed the bis-phosphite ligands employable herein would yield a diphenolic compound in which each phenolic oxygen atom is bonded to a separate aryl radical as well as a different or same organic diol and the equivalent of two mono-ol compounds.

The subject invention encompasses the carrying out of any known carbonylation process in which the catalyst thereof is replaced by a Group VIII transition metal-bis-phosphite complex catalyst as disclosed herein. As noted above such carbonylation reactions may involve the reaction of organic compounds with carbon monoxide, or carbon monoxide and a third reactant e.g. hydrogen in the presence of a catalytic amount of a Group VIII transition metal-bis-phosphite ligand complex catalyst, said ligand being of the general Formula (I) above.

More preferably the subject invention involves the use of such a Group VIII transition metal-bis-phosphite ligand complex catalyst and free bis-phosphite ligand in the production of aldehydes wherein an olefinic compound is reacted with carbon monoxide and hydrogen. The aldehydes produced correspond to the compounds obtained by the addition of a carbonyl group to an olefinically unsaturated carbon atom in the starting material with simultaneous saturation of the olefinic bond. Such preferred processes are known in industry under varying names such as the oxo process or reaction, oxonation, the Roelen reaction and more commonly hydroformylation. Accordingly, the processing techniques of this invention may correspond to any of the known processing techniques heretofore employed in conventional carbonylation and especially hydroformylation reactions.

For instance, the preferred hydroformylation process can be conducted in continuous, semi-continuous, or batch fashion and involve a liquid recycle and/or gas recycle operation as desired. Likewise, the manner or order of addition of the reaction ingredients, catalyst and solvent are also not critical and may be accomplished in any conventional fashion.

In general, the preferred hydroformylation reaction is preferably carried out in a liquid reaction medium that contains a solvent for the catalyst, preferably one in which both the olefinically unsaturated compound and catalyst are substantially soluble. In addition, as is the case with prior art hydroformylation processes that employ a rhodium-phosphorus complex catalyst and free phosphorus ligand, it is highly preferred that the hydroformylation process of this invention be effected in the presence of free bis-phosphite ligand as well as in the presence of the complex catalyst. By "free ligand" is meant bis-phosphite ligand that is not complexed with the Group VIII transition metal atom in the active complex catalyst.

The more preferred hydroformylation process of this invention is an improved selective hydroformylation relating to the production of aldehydes having very high normal to iso(branched) product ratios.

The Group VIII transition metals which make up the metal-bis-phosphite complexes of this invention include those selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being Rh, Co, Ir and Ru, more preferably Rh and Co, especially Rh. It is to be noted that the successful practice of this invention does not depend and is not predicated on the exact structure of the catalytically active metal complex species, which may be present in their mononuclear, dinuclear and or higher nuclearity forms. Indeed the exact active structure is not known. Although it is not intended herein to be bound to any theory or mechanistic discourse, it appears that the active catalytic species may in its simplest form consist essentially of the Group VIII transition metal in complex combination with the carbon monoxide and a bis-phosphite ligand.

The term "complex" as used herein and in the claims means a coordination compound formed by the union of one or more electronically rich molecules or atoms capable of independent existence with one or more electronically poor molecules or atoms, each of which is also capable of independent existence. The bis-phosphite ligands employable herein which possess two phosphorus donor atoms each having one available or unshared pair of electrons which are each capable of forming a coordinate covalent bond independently or in concert (e.g. via chelation) with the Group VIII transition metal. As can be surmised from the above discussion, carbon monoxide (which is also properly classified as a ligand) is also present and complexed with the Group VIII transition metal. The ultimate composition of the active complex catalyst may also contain an additional ligand e.g. hydrogen or an anion satisfying the coordination sites or nuclear charge of the Group VIII transition metal as in the case of heretofore conventional Group VIII transition metal-triorganophosphine or phosphite catalysts. Illustrative additional ligands include e.g., halogen (Cl, Br, I), alkyl, aryl, substituted aryl, $CF_3$, $C_2F_5$, CN, $R_2PO$ and RP(O)(OH) O (wherein each R is alkyl or aryl), acetate, acetylacetonate, $SO_4$, $PF_4$, $PF_6$, $NO_2$, $NO_3$, $CH_3O$, $CH_2=CHCH_2$, $C_6H_5CN$, $CH_3CH$, NO, $NH_3$, pyridine, $(C_2H_5)_3N$, mono-olefins, diolefins and triolefins, tetrahydrofuran, and the like. It is of course to be understood that the active complex species is preferably free of any additional organic ligand or anion that might poison the catalyst and have an undue adverse effect on catalyst performance. For instance it is known that in conventional rhodium catalyzed hydroformylation reactions that halogen anions and sulfur compounds can poison the catalyst. Accordingly it is preferred that in the rhodium catalyzed hydroformylation reactions of this invention that the active catalysts also be free of halogen and sulfur directly bonded to the rhodium, although such may not be absolutely necessary.

The number of available coordination sites on such Group VIII transition metals is well known in the art and may range in number from 4 to 6. Thus the active species may comprise a complex catalyst mixture, in their monomeric, dimeric or higher nuclearity forms, which are characterized by at least one bis-phosphite molecule complexed per one molecule of rhodium. As noted above carbon monoxide is also considered to be present and complexed with the rhodium in the active species. Moreover, as in the case of conventional rhodium-triorganophosphine or phosphite ligand complexed catalyzed hydroformylation reactions, the active catalyst species of which is generally considered to also contain hydrogen directly bonded to the rhodium, it is likewise considered that the active species of the preferred rhodium catalyst employed in this invention during hydroformylation may also be complexed with hydrogen in addition to the bis-phosphite and carbon monoxide ligands in view of the hydrogen gas employed by the process.

Moreover, regardless of whether one preforms the active complex catalyst prior to introduction into the carbonylation reaction zone or whether the active species is prepared in situ during the carbonylation reaction, it is preferred that the carbonylation, and especially the hydroformylation reaction be effected in the presence of free bis-phosphite ligand, although such may not be absolutely necessary.

The bis-phosphite ligands employable in this invention as noted above are those having the general formula

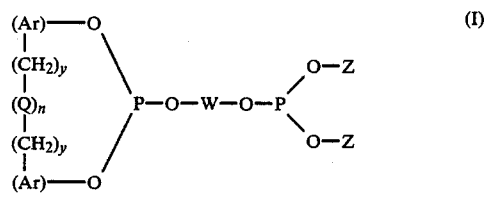

(I)

wherein each Ar group represents an identical or different substituted or unsubstituted aryl radical; wherein W represents a divalent radical selected from the group consisting of alkylene, arylene and —arylene—($CH_2$)y—(Q—)$_n$—($CH_2$)y—arylene—, wherein each arylene radical is the same as Ar defined above; wherein each y individually has a value of 0 or 1; wherein each Q individually represents a divalent bridging group selected from the class consisting of —$CR^1R^2$—, —O—, —S—, —$NR^3$—, and —CO—, wherein each $R^1$ and $R^2$ radical individually represents a radical selected from the group consisting of hydrogen, alkyl of 1 to 12 carbon atoms, phenyl, tolyl and anisyl, wherein each $R^3$, $R_4$, and $R^5$ radical individually represents —H or —$CH_3$; wherein each n individually has a value of 0 or 1; and wherein each Z group individually represents a monovalent hydrocarbon radical selected from the group consisting of substituted or unsubstituted alkyl, aryl, alkaryl, aralkyl and alicyclic radicals. Preferably each y and each n has a value of 0. Moreover, when either n is 1, its corresponding Q is preferably a —$CR^1R^2$ bridging group as defined above and more preferably methylene (—$CH_2$—) or alkylidene (—$CHR^2$—), wherein $R^2$ is an alkyl radical of 1 to 12 carbon atoms, (e.g. methyl, ethyl, propyl, isopropyl, butyl, isodecyl, dodecyl, etc., especially methyl).

Illustrative monovalent hydrocarbon radicals represented by the Z groups in the above bis-phosphite formulae include substituted or unsubstituted monovalent hydrocarbon radicals containing from 1 to 30 carbon atoms selected from the group consisting of substituted or unsubstituted alkyl, aryl, alkaryl, aralkyl and alicyclic radicals. While each Z group in a given phosphite may be individually the same or different, preferably they are both the same.

More specific illustrative monovalent hydrocarbon radicals represented by Z include primary, secondary and tertiary chain alkyl radicals such as methyl, ethyl, propyl, isopropyl, butyl, sec-butyl, t-butyl, neo-pentyl, sec-amyl, t-amyl, iso-octyl, 2-ethylhexyl, iso-nonyl, iso-decyl, octadecyl, and the like; aryl radicals, such as phenyl, naphthyl, anthracyl, and the like; aralkyl radicals, such as benzyl, phenylethyl, and the like; alkaryl radicals, such as tolyl, xylyl, p-alkylphenyls, and the like; and alicyclic radicals such as cyclopentyl, cyclohexyl, cyclooctyl, cyclohexylethyl, 1-methylcyclohexyl, and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms. Among the more preferred Z radicals are phenyl and substituted phenyl radicals.

Illustrative divalent arylene radicals represented by W in the above bis-phosphite formula include substituted and unsubstituted radicals selected from the group consisting of alkylene, phenylene, naphthylene, —phenylene—($CH_2$)y(Q)$_n$—($CH_2$)y—phenylene— and —naphthylene—($CH_2$)y(Q)$_m$($CH_2$)y—naphthylene—radicals, wherein Q, n and y are the same as defined above. More specific illustrative divalent radicals represented by W include e.g. 1,2-ethylene, 1,3-propylene, 1,6-hexylene, 1,8-octylene, 1,12-dodecylene, 1,4-phenylene, 1,8-naphthylene, 1,1'-biphenyl-2,2'-diyl, 1,1'-binaphthyl-2,2'-diyl, 2,2'-binaphthyl-1,1'-diyl, and the like. The alkylene radicals may contain from 2 to 12 carbon atoms, while the arylene radicals may contain from 6 to 18 carbon atoms. Preferably W is an arylene radical and more preferably W is a substituted 1,1'-biphenyl-2,2'-diyl radical.

Illustrative aryl radicals represented by the Ar groups and the arylene radicals of W in the above bis-phosphite formula include both substituted and unsubstituted aryl radicals. Such aryl radicals may contain from 6 to 18 carbon atoms such as phenylene ($C_6H_4$), naphthylene ($C_{10}H_6$), anthracylene ($C_{14}H_8$), and the like.

Illustrative substituent groups that may be present on the monovalent hydrocarbon radicals represented by Z as well as the arylene radicals of W and the aryl groups represented by Ar in the above diorganophosphite formula include monovalent hydrocarbon radicals such as the same type of substituted or unsubstituted alkyl, aryl, alkaryl, aralkyl and alicyclic radicals mentioned above for Z, as well as silyl radicals such as —Si($R^6$)$_3$ and —Si(O$R^6$)$_3$, amino radicals such as —N($R^6$)$_2$, acyl radicals such as —C(O)$R^6$, carbonyloxy radicals such as —C(O)O$R^6$, oxycarbonyl radicals such as —OC(O)$R^6$, amido radicals such as —C(O)N($R^6$)$_2$ and —N($R^6$)-C(O)$R^6$, sulfonyl radicals such as —S(O)$_2R^6$, sulfinyl radicals such as —S(O)$R^6$, ether (e.g. alkoxy) radicals such as —O$R^6$, thionyl ether radicals such as —S$R^6$, phosphonyl radicals such as —P(O)($R^6$)$_2$, and halogen, nitro, cyano, trifluoromethyl and hydroxy radicals, and the like, wherein each $R^6$ individually represents the same or different, substituted or unsubstituted monovalent hydrocarbon radical having the same meaning as defined herein with the proviso that in amino substituents such as —N($R^6$)$_2$, each $R^6$ taken together can also represent a divalent bridging group that forms a heterocyclic radical with the nitrogen atom and in amino and amido substituents such as —N($R^6$)$_2$, —C(O)N($R^6$)$_2$ and —N($R^6$)C(O)$R^6$ each —$R^6$ bonded to N can also be hydrogen, while in phosphonyl substituents such as —P(O)($R^6$)$_2$, one $R^6$ radical can also be hydrogen. Preferably the monovalent hydrocarbon substituent radicals, including those represented by $R^6$, are unsubstituted alkyl or aryl radicals, although if desired they in turn may be substituted with any substituent which does not unduly adversely effect the process of this invention, such as e.g. those hydrocarbon and non-hydrocarbon substituent radicals already herein outlined above.

Among the more specific unsubstituted monovalent hydrocarbon substitute radicals, including those represented by $R^6$, that may be bonded to the monovalent hydrocarbon radicals represented by Z and/or the arylene radicals of W and/or the Ar groups of the above diorganophosphite formula that may be mentioned are alkyl radicals including primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and the like; aryl radicals such as phenyl, naphthyl and the like; aralkyl radicals such as benzyl, phenylethyl, triphenylmethyl, and the like; alkaryl radicals such as tolyl, xylyl, and the like; and alicyclic radicals such as cyclopentyl, cyclohexyl, 1-methylcyclohexyl, cyclooctyl, cyclohexylethyl, and the like. More specific illustrative non-hydrocarbon substituents that may be present on the monovalent hydrocarbon radicals represented by Z and/or the arylene radicals of W and/or the Ar groups of the above diorganophosphite formula include e.g. halogen, preferably chlorine or fluorine, —NO$_2$, —CN, —CF$_3$, —OH, —Si(CH$_3$)$_2$, —Si(OCH$_3$)$_3$, —Si(C$_3$H$_7$)$_3$, —C(O)CH$_3$, —C(O)C$_2$H$_5$, —OC(O)C$_6$H$_5$, —C(O)OCH$_3$, —N(CH$_3$)$_2$, —NH$_2$, —NHCH$_3$, —NH(C$_2$H$_5$), —CONH$_2$, —CON(CH$_3$)$_2$, —S(O)$_2$C$_2$H$_5$, —OCH$_3$, —OC$_2$H$_5$, —OC$_6$H$_5$, —C(O)C$_6$H$_5$, —O(t—C$_4$H$_9$), —SC$_2$H$_5$, —OCH$_2$CH$_2$OCH$_3$, —(OCH$_2$CH$_2$)$_2$OCH$_3$, —(OCH$_2$CH$_2$)$_3$OCH$_3$, —SCH$_3$, —S(O)CH$_3$, —SC$_6$H$_5$, —P(O)(C$_6$H$_5$)$_2$, —P(O)(CH$_3$)$_2$, —P(O)(C$_2$H$_5$)$_2$, —P-(O)(C$_3$H$_7$)$_2$, —P(O)(C$_4$H$_9$)$_2$, —P(O)(C$_6$H$_{13}$)$_2$, —P-(O)CH$_3$(C$_6$H$_5$), ( —P(O)(H)(C$_6$H$_5$), —NHC(O)CH$_3$,

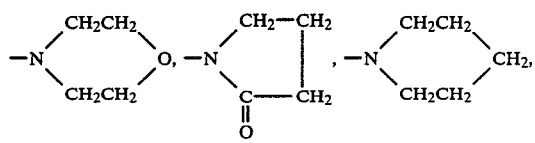

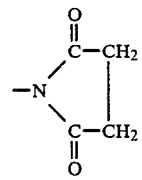

and the like. In general, the substituent radicals present on the monovalent hydrocarbon radicals represented by Z and the arylene radicals of W and the Ar groups of the above diorganophosphite formula may also contain from 1 to 18 carbon atoms and may be bonded to the monovalent hydrocarbon radicals represented by Z and/or such arylene radicals of W and/or such Ar groups in any suitable position as may be the bridging group —(CH$_2$)$_6$—(Q)$_n$—(CH$_2$)$_y$— connecting the two arylene groups of W or the Ar groups of the above formula. Moreover, each Ar radical and/or radical represented by Z and/or arylene radical of W may contain one or more such substituent groups which substituent groups may also be the same or different in any given diorganophosphite. Preferred substituent radicals include alkyl and alkoxy radicals containing from 1 to 18 carbon atoms and more preferably from 1 to 10 carbon atoms, especially t-butyl and methoxy radicals.

Among the more preferred bis-phosphite ligands are those wherein the two Ar groups linked by the bridging group represented by —(CH$_2$)$_y$—(Q)$_n$—(CH$_2$)$_y$— in the above bis-phosphite formula are bonded through their ortho positions in relation to the oxygen atoms that connect the Ar groups to the phosphorus atom. It is also preferred that any substituent radical, when present on such Ar groups be bonded in the para and/or ortho position of the aryl in relation to the oxygen atom that bonds the given substituted aryl group to its phosphorus atom.

Accordingly, a preferred class of bis-phosphite ligands employable in this invention are those of the formulas

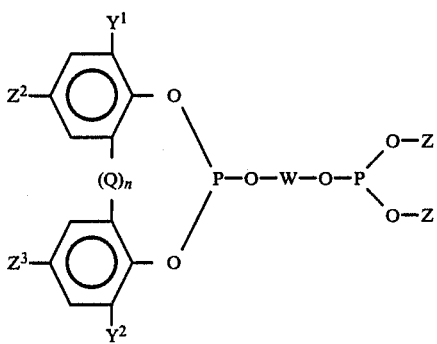
(II)

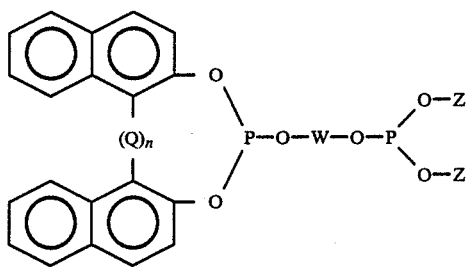
(III)

wherein in said Formulas (II) and (III), Q is —$CR^1R^2$ wherein each $R^1$ and $R^2$ radical individually represents a radical selected from the group consisting of hydrogen, alkyl of 1 to 12 carbon atoms (e.g. methyl, propyl, isopropyl, butyl, isodecyl, dodecyl, etc.) phenyl, tolyl and anisyl, and n has a value of 0 to 1; wherein each $Y^1$, $Y^2$, $Z^2$, and $Z^3$ group individually represents a radical selected from the group consisting of hydrogen, an alkyl radical having from 1 to 18 carbon atoms, substituted or unsubstituted aryl, alkaryl, aralkyl and alicyclic radicals as defined and exemplified herein above (e.g. phenyl, benzyl, cyclohexyl, 1-methylcyclohexyl, and the like) cyano, halogen, nitro, trifluoromethyl, hydroxy, as well as the carbonyloxy, amino, acyl, phosphonyl, oxycarbonyl, amido, sulfinyl, sulfonyl, silyl, alkoxy, and thionyl as defined and exemplified herein above, and wherein W and Z are the same as defined above. Preferably both $Y^1$ and $Y^2$ are radicals having a steric hindrance of methyl, or more preferably isopropyl, or greater. Preferably Q represents a methylene (—$CH_2$—) bridging group or an alkylidene (—CH-$R^2$—) bridging group wherein $R^2$ is an alkyl radical of 1 to 12 carbon atoms as defined above, especially methyl (e.g. —$CHCH_2$—). The more preferred ligands are those of Formula (II) above, wherein, both $Y^1$ and $Y^2$ are branched chain alkyl radicals having three to five carbon atoms, especially t-butyl, and $Z^2$ and $Z^3$ are hydrogen, an alkyl radical, especially t-butyl, a hydroxy radical or an alkoxy radical, especially methoxy. More preferably each Z group is an aryl radical of the formula

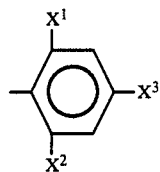

wherein each $X^1$, $X^2$ and $X^3$ radical individually represents a radical selected from the group consisting of hydrogen, tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, 2-ethylhexyl, nonyl, decyl, dodecyl, octadecyl, and the like, as well as, substituted and unsubstituted aryl, alkaryl, aralkyl and alicyclic radicals (e.g. phenyl, benzyl, cyclohexyl, 1-methylcyclohexyl, and the like), and cyano, halogen, nitro, trifluoromethyl, hydroxy, amino, acyl, carbonyloxy, oxycarbonyl, amido, sulfonyl, sulfinyl, silyl, alkoxy, phosphonyl, and thionyl radicals as defined and exemplified above.

Further more preferred bis-phosphite ligands include those wherein W in the above bisphosphite formulas is a divalent radical selected from the group consisting of substituted or unsubstituted naphthylene, —naphthylene—$(Q)_n$—naphthylene—and—phenylene—$(Q)_n$—phenylene—radicals wherein Q and n are the same as both generically and preferably defined above. Among the more preferred bis-phosphite ligands are those wherein the divalent naphthylene radical represented by W is selected from the group consisting of 1,2naphthylene, 2,3-naphthylene and especially 1,8-naphthylene and those wherein the two phenylene radicals or two naphthylene radicals of W linked by the bridging group represented by —$(Q)_n$— are bonded through their ortho positions in relation to the oxygen atoms that connect the two phenylene or two naphthylene radicals to their phosphorus atom. It is also preferred that any substituent radical when present on such phenylene or naphthylene radicals be bonded in the para and/or ortho position of the phenylene or naphthylene radical in relation to the oxygen atom that bonds the given substituted phenylene or naphthylene radical to its phosphorus atom.

Accordingly, another preferred class of bisphosphite ligands employable herein are those of the formulas

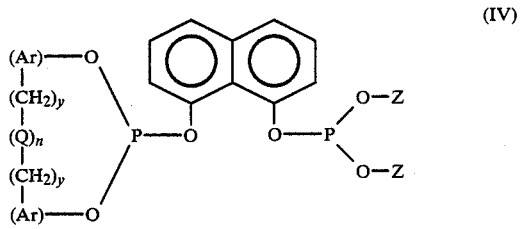
(IV)

wherein Ar, Q, Z, y and n are the same as generically and preferably defined above and

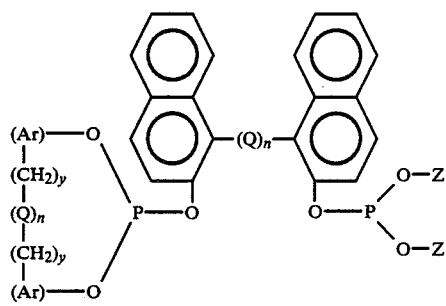
(V)

wherein Ar, Q, Z, y and n are the same as generically and preferably defined above; and

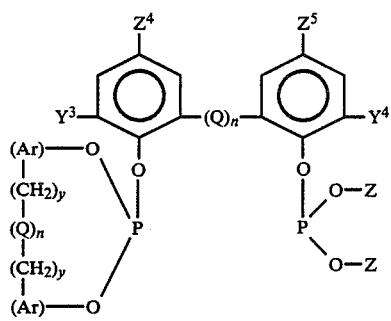
(VI)

wherein Ar, Q, Z, y and n are the same as generically and preferably defined above and wherein each $Y^3$ $Y^4$, $Z^4$ and $Z^5$ group individually represents a radical selected from the group consisting of hydrogen, an alkyl radical having from 1 to 18 carbon atoms, substituted or unsubstituted aryl, alkaryl, aralkyl and alicyclic radicals as defined and exemplified herein above (e.g. phenyl, benzyl, cyclohexyl, 1-methylcyclohexyl, and the like), cyano, halogen, nitro, trifluoromethyl, hydroxy, as well as the carbonyloxy, amino, acyl, phosphonyl, oxycarbonyl, amido, sulfinyl, sulfonyl, silyl, alkoxy, and thionyl radicals as defined and exemplified herein above.

Preferably both $Y^3$ and $Y^4$ are radicals having a steric hindrance of methyl, or more preferably isopropyl, or greater. The more preferred ligands are those of Formula (VI) above, wherein both $Y^3$ and $Y^4$ are branched chain alkyl radicals having three to five carbon atoms, especially t-butyl, and $Z^4$ and $Z^5$ are hydrogen, an alkyl radical especially t-butyl, a hydroxy radical or an alkoxy radical, especially methoxy.

Among the more preferred bis-phosphites represented by Formulas (IV), (V) and (VI) above are those having the formulas

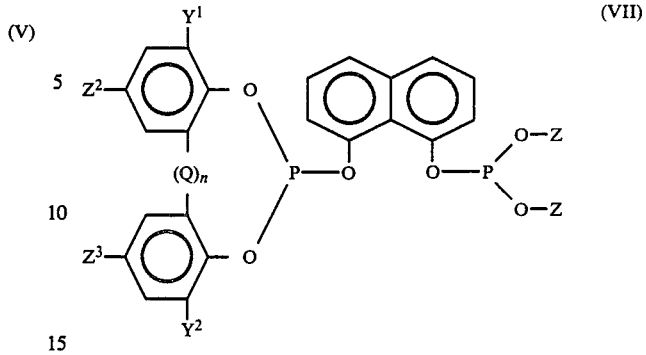
(VII)

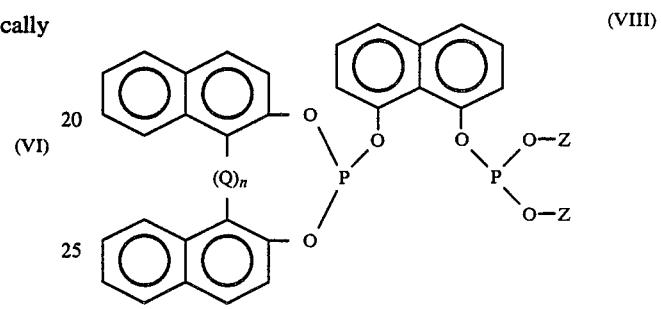
(VIII)

wherein in said Formulas (VII) and (VIII), $Y^1$, $Y^Z$, Q, Z, $Z^2$, $Z^3$, and n are the same as generically and preferably defined in Formulas (II), (III) and (IV) above, and most preferably n is zero; and as well as those having the formulas

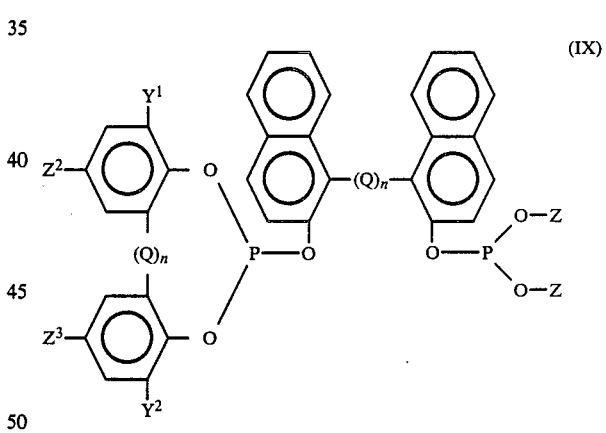
(IX)

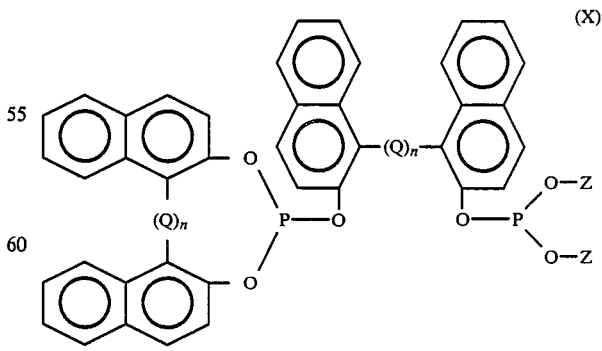
(X)

wherein in said Formulas (IX) and (X), $Y^1$, $Y^2$, Q, Z, $Z^2$, $Z^3$ and n are the same as generically and preferably defined in Formulas (II), (III) and (V) above, must preferably n is zero; and as well as those having the formulas

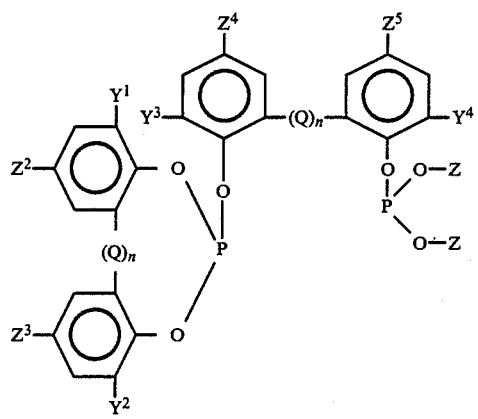
(XI)

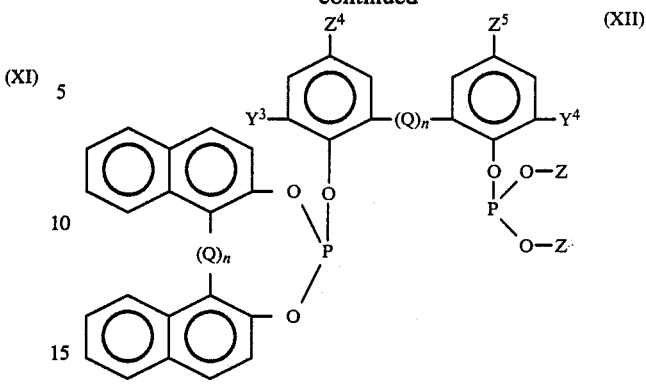
(XII)

wherein in said Formulas (XI) and (XII), $Y^1$, $Y^2$, $Y^3$, $Y^4$, Z, $Z^2$, $Z^3$, $Z^4$, $Z^5$, Q and n are the same as generically and preferably defined above in Formulas (II), (V) and (VI) above.

The most preferred bis-phosphite ligands of this invention are those of Formula XI above.

Additional illustrative examples of the bis-phosphite ligands of this invention include e.g.

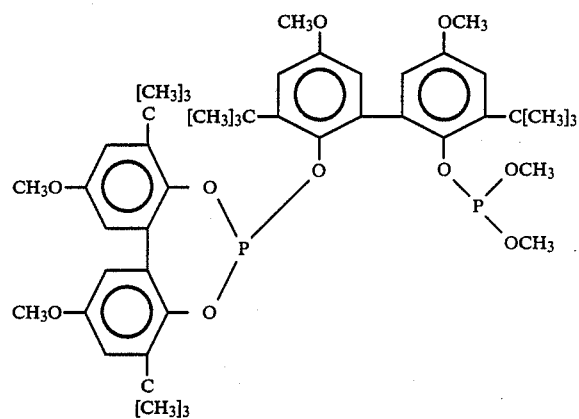

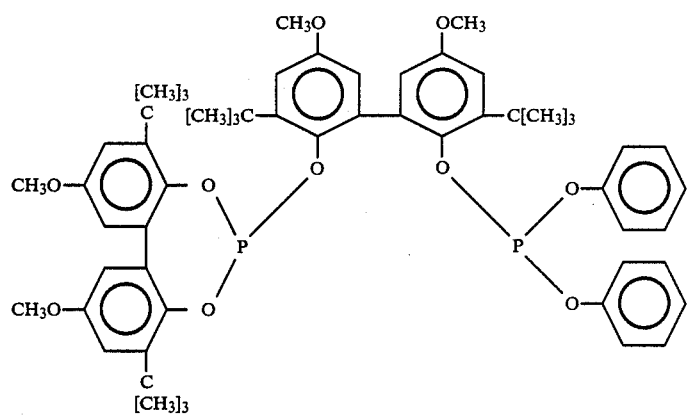

-continued
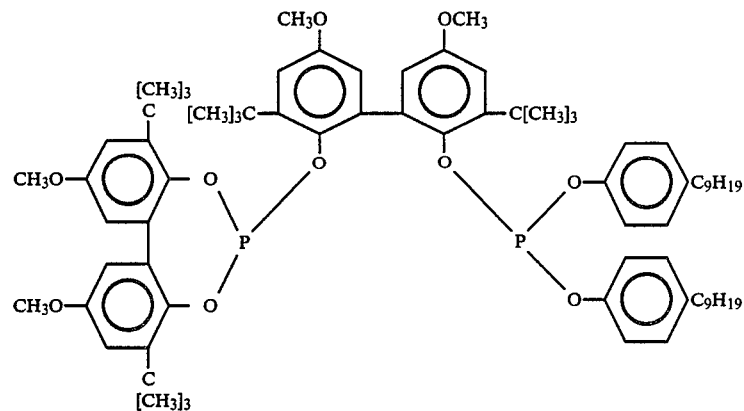
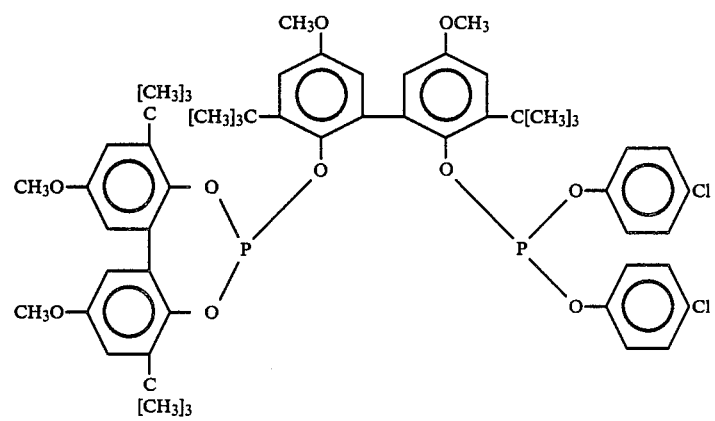
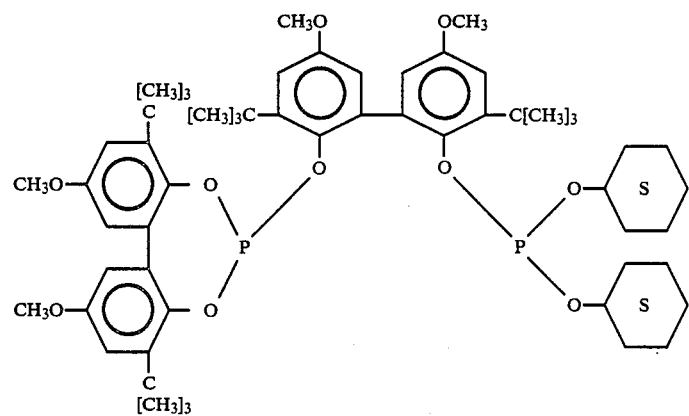

-continued
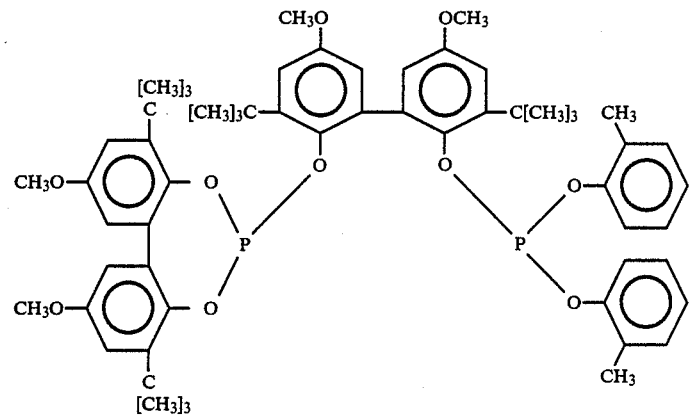
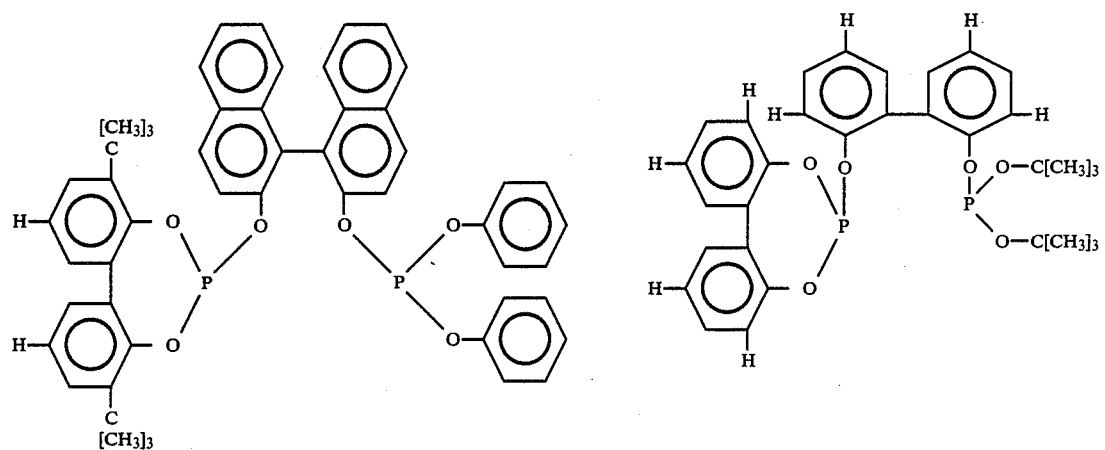
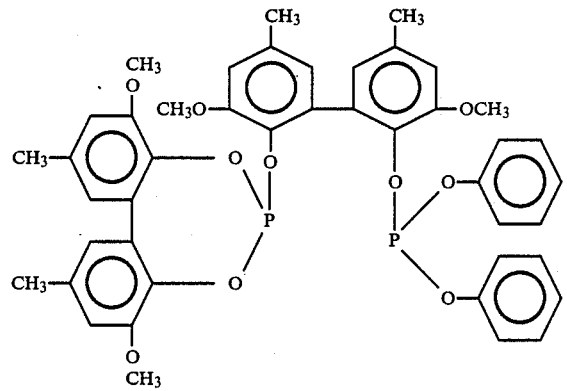

-continued
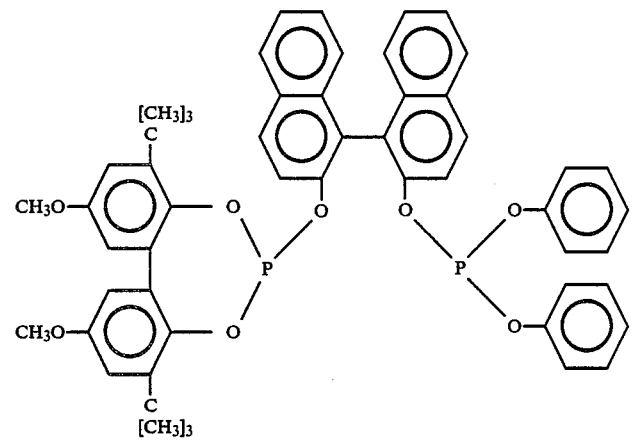
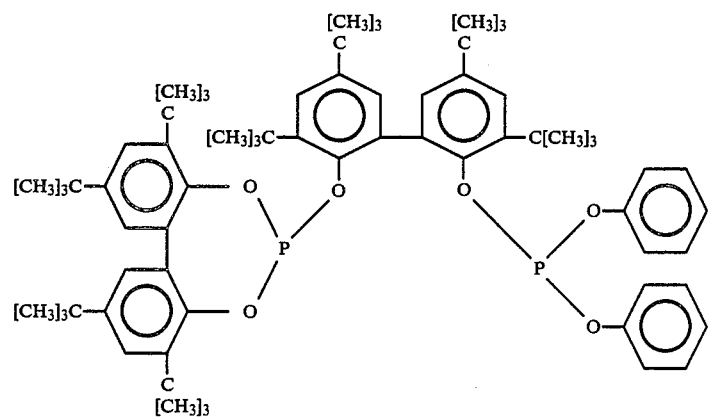
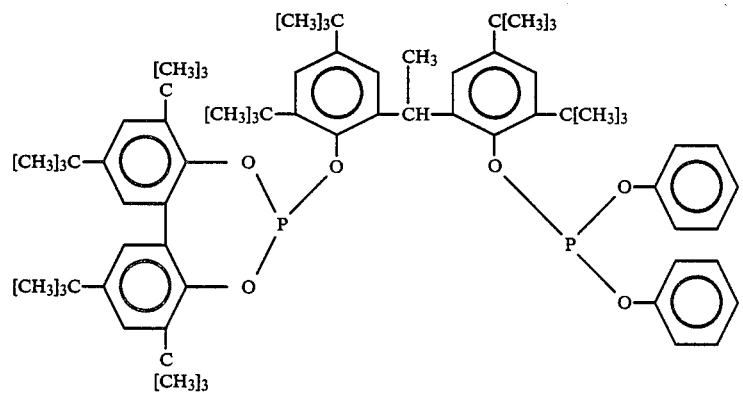

-continued
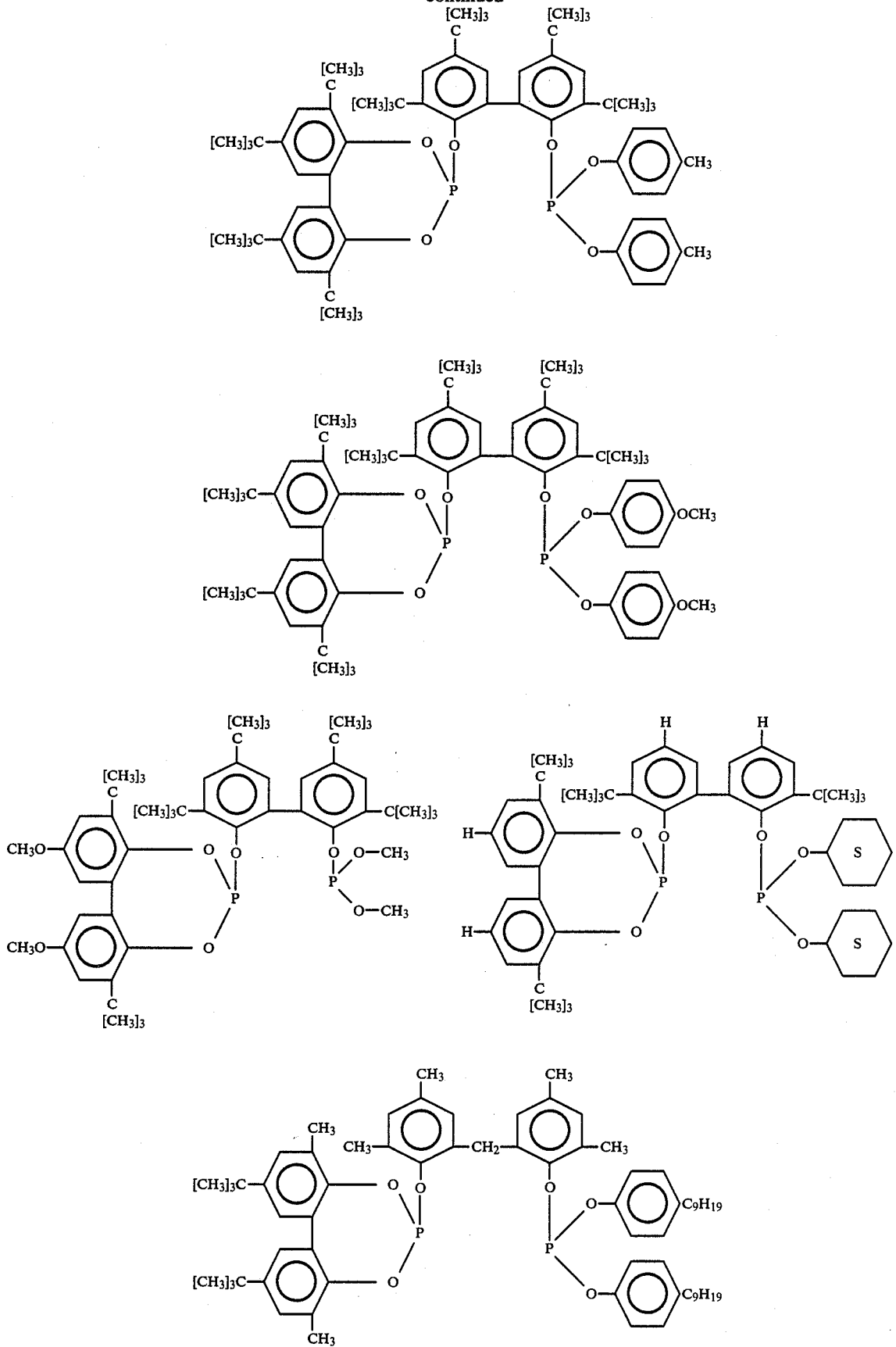

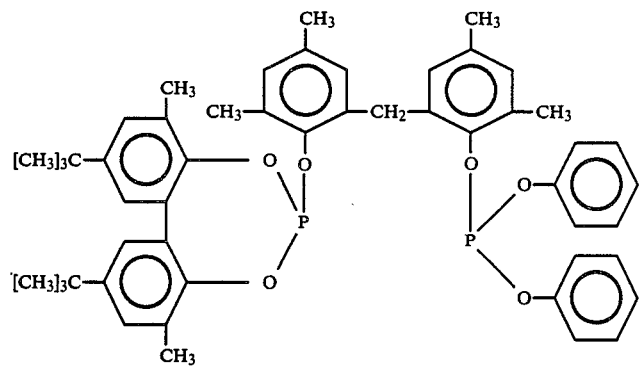
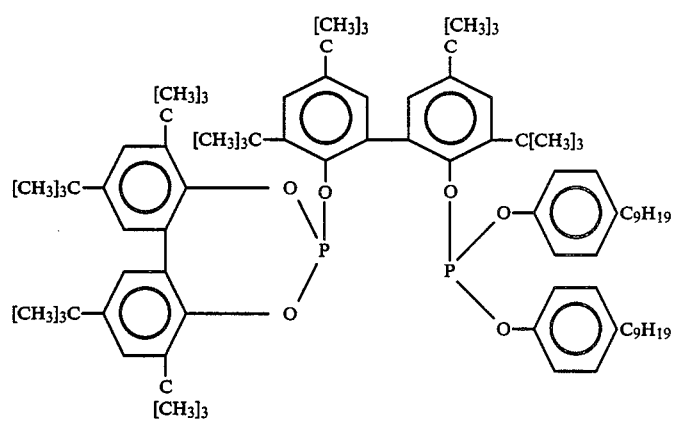
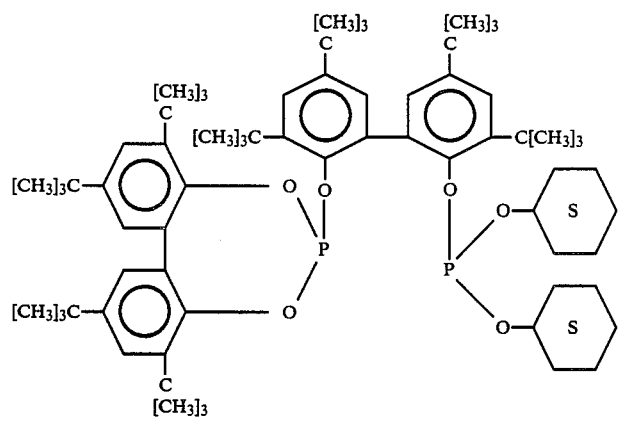
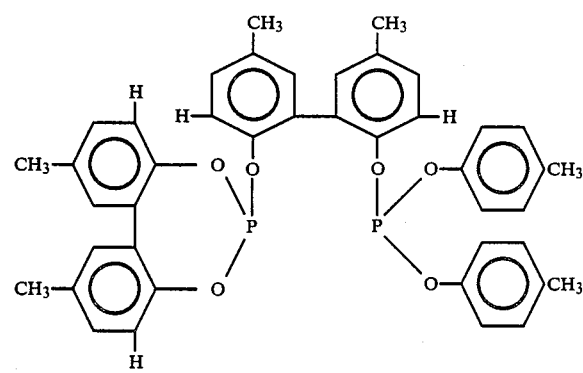

-continued
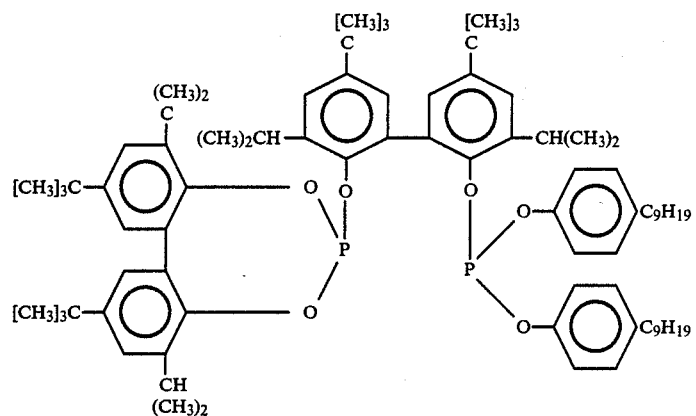
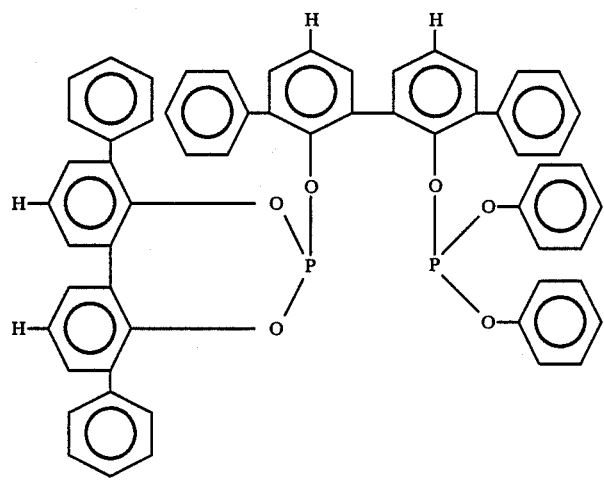
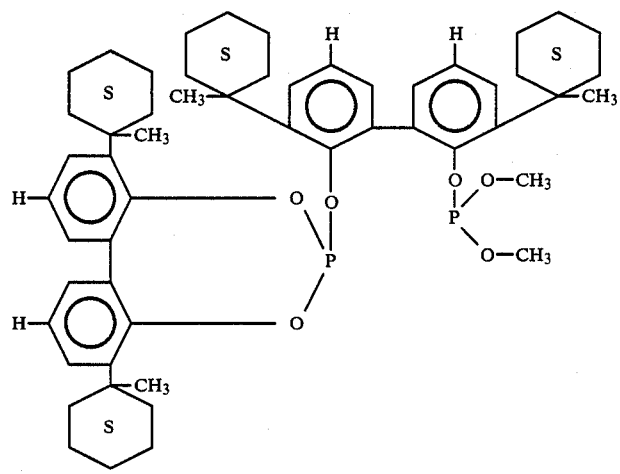

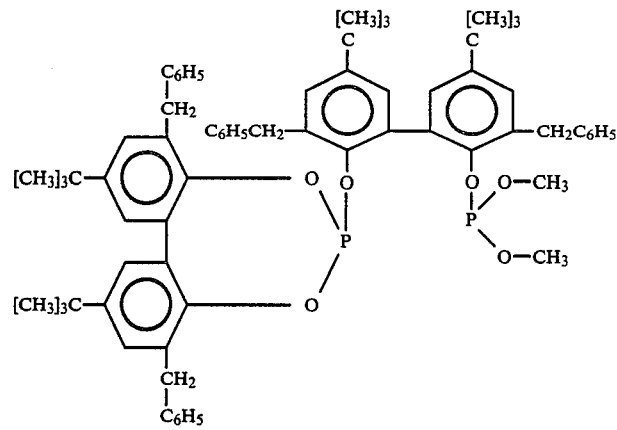
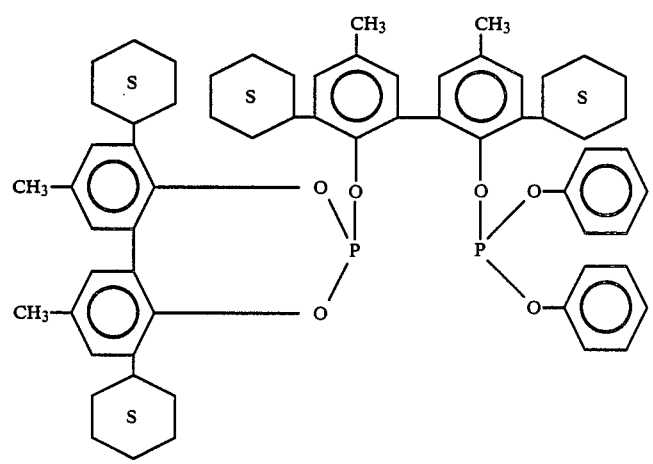
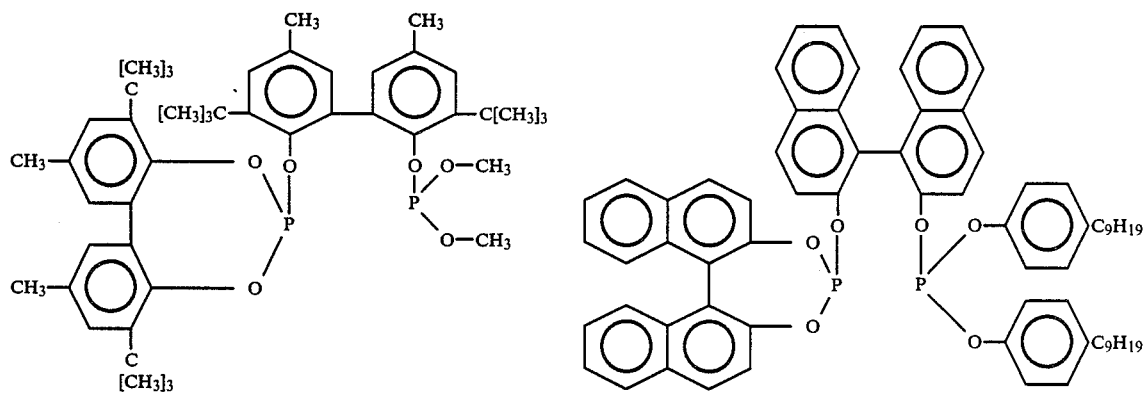

-continued
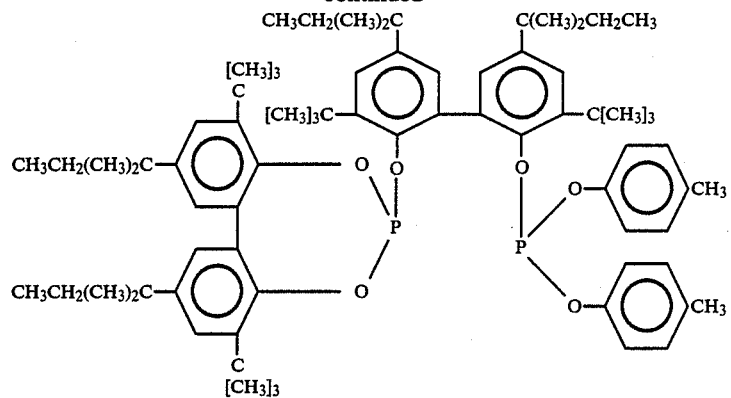
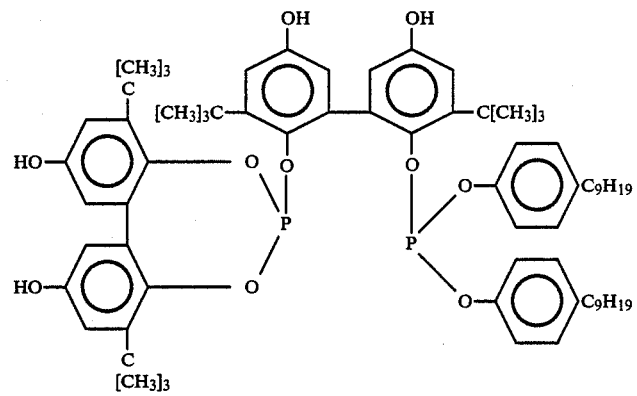
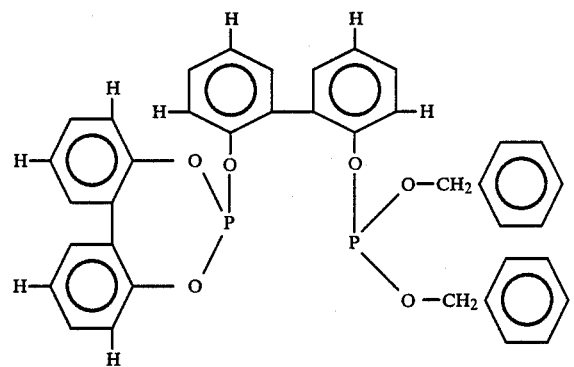
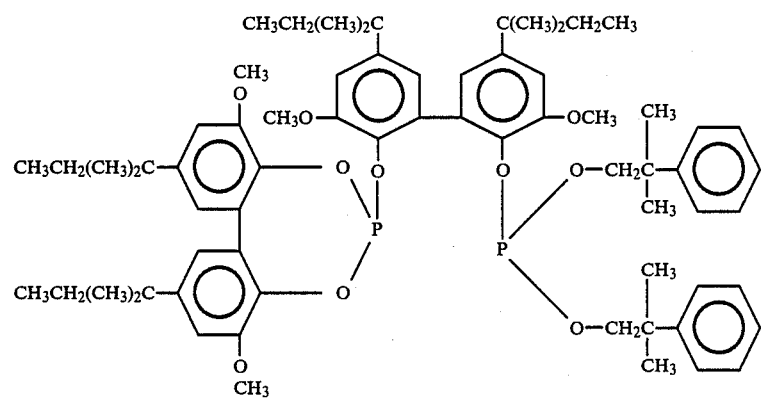

-continued
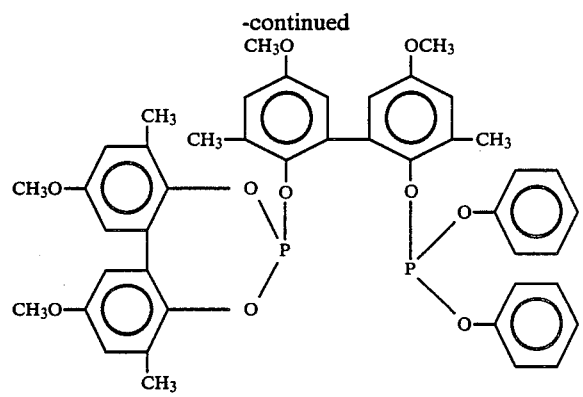
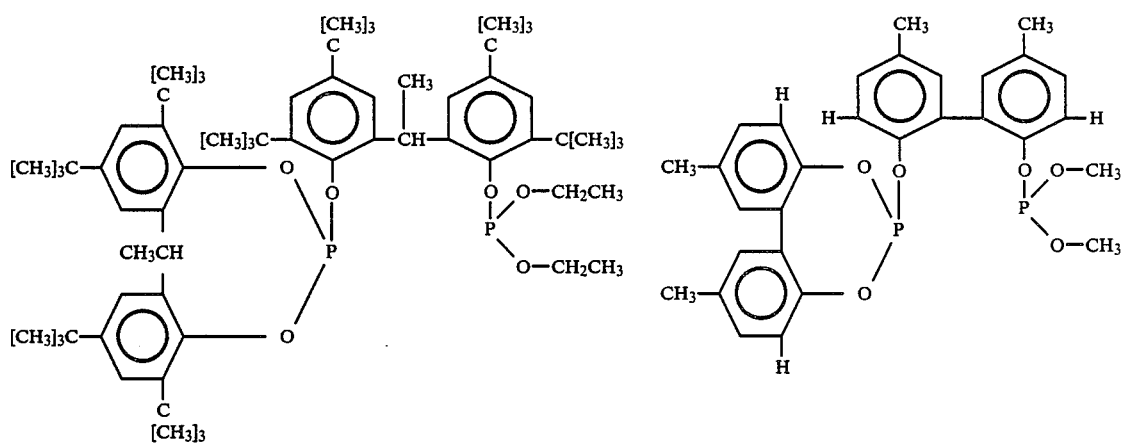
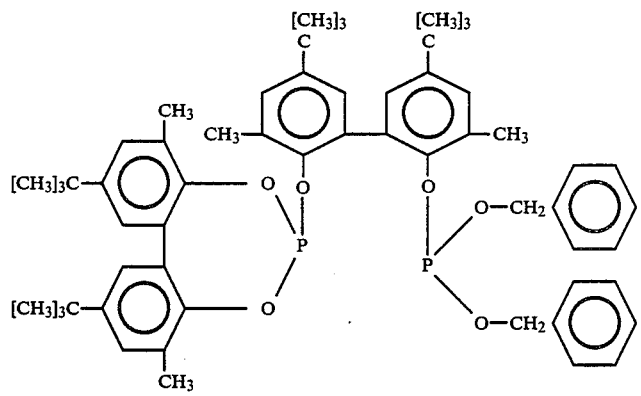
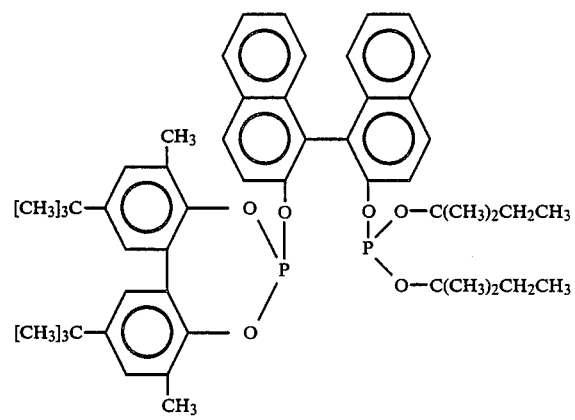

-continued
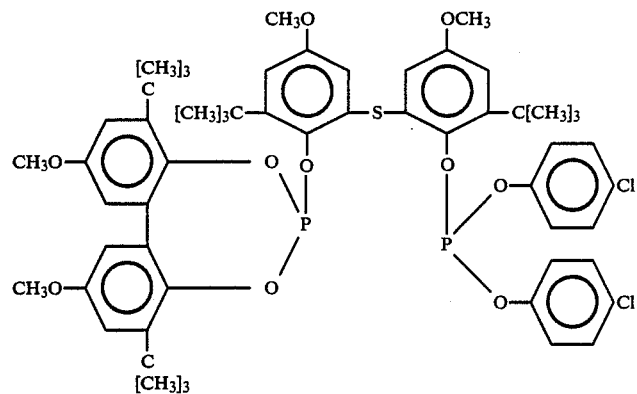
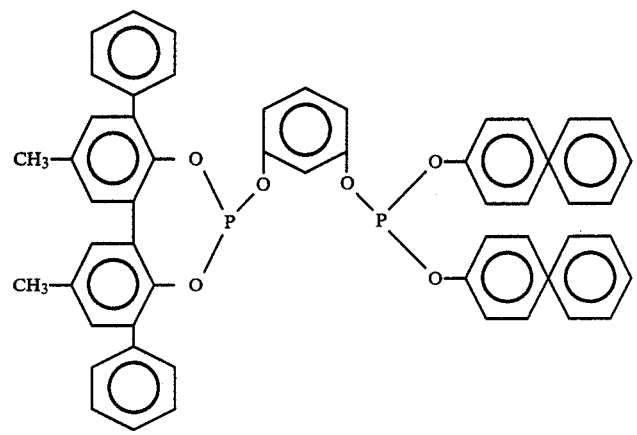
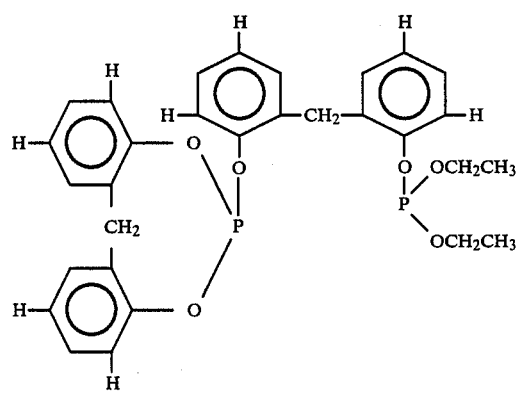
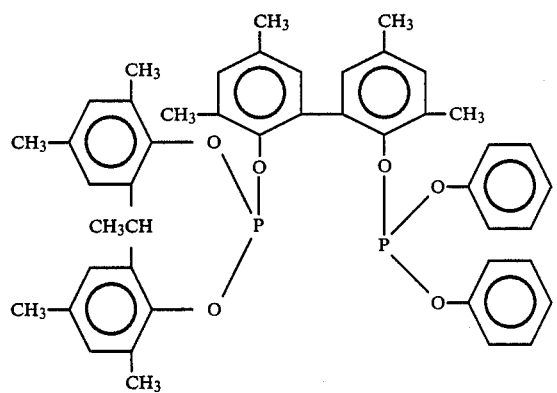

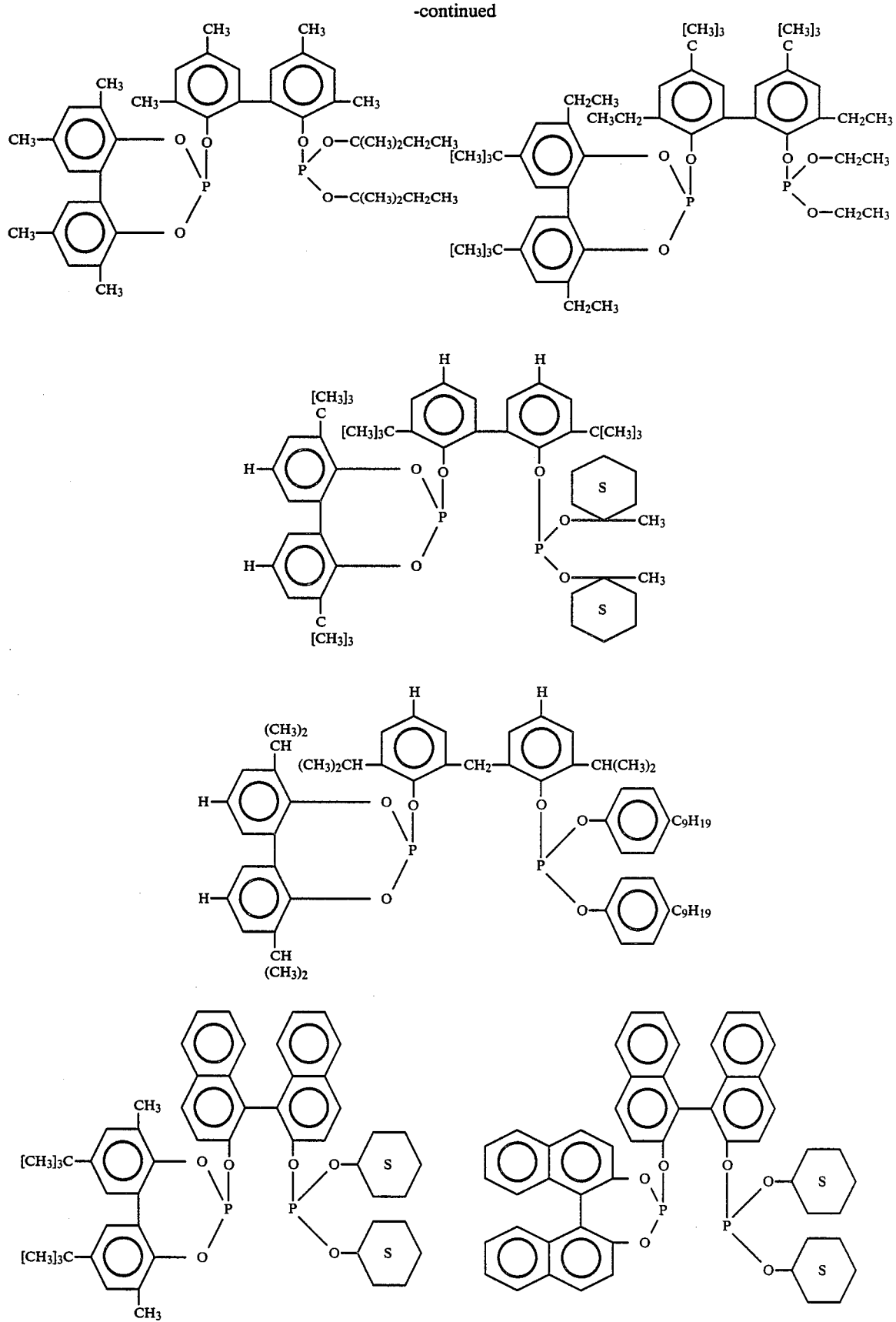

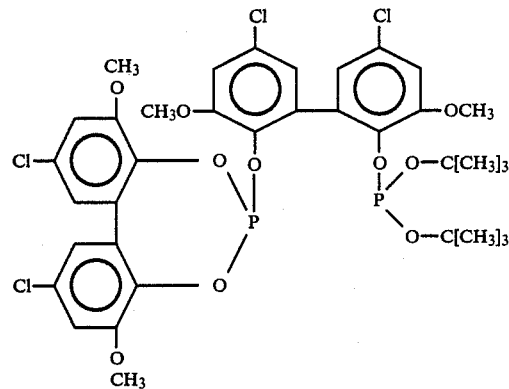
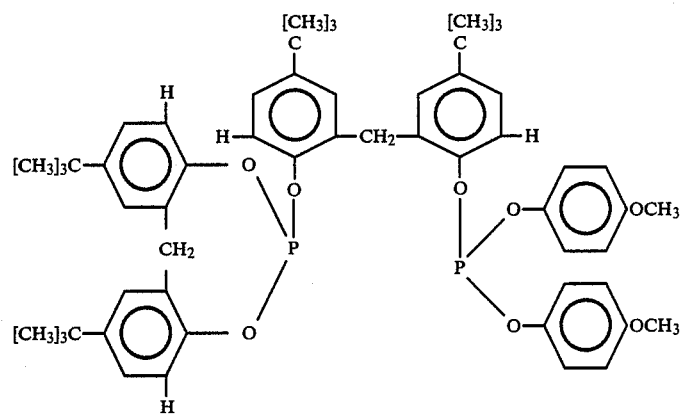
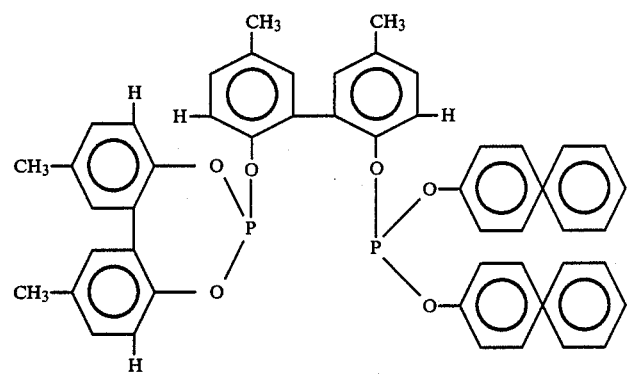

-continued
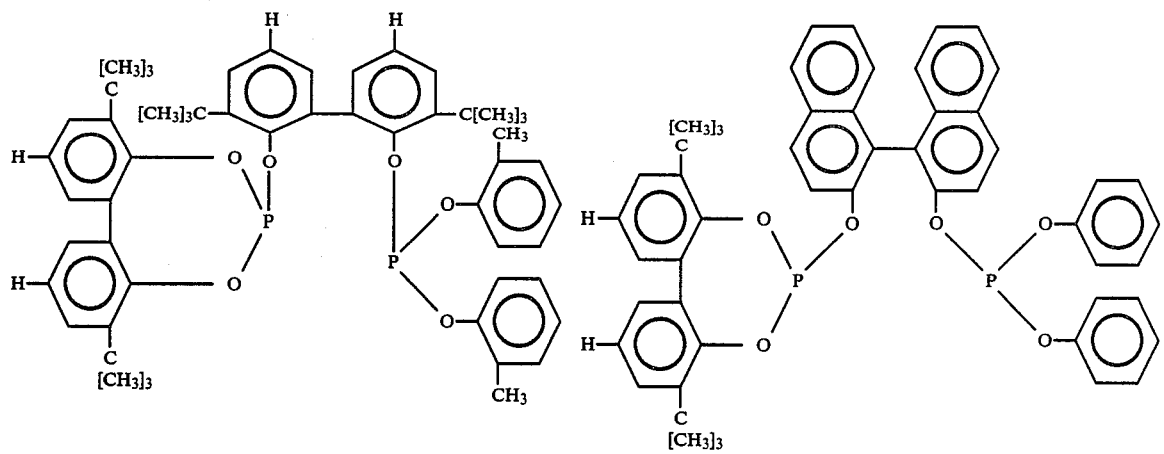
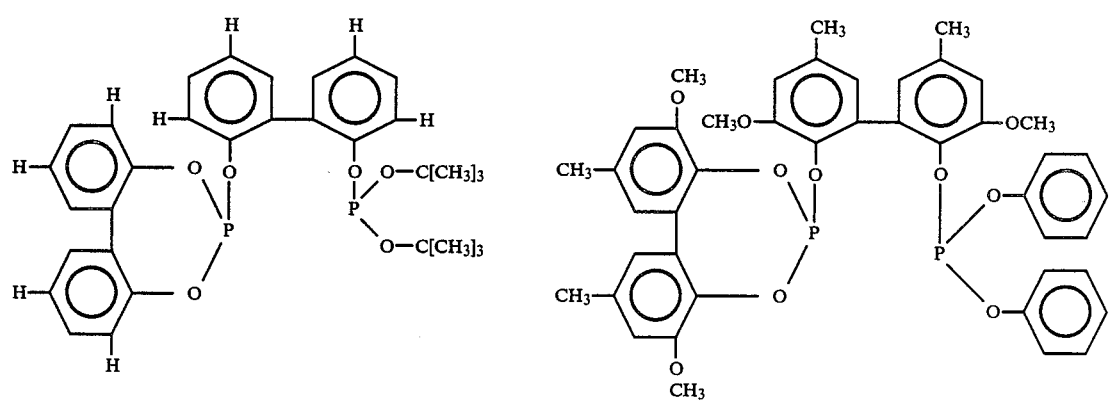
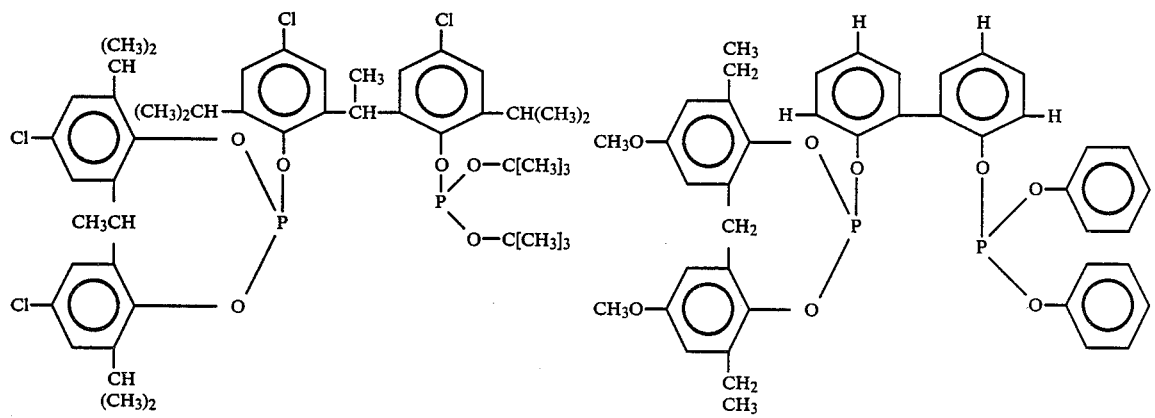

-continued
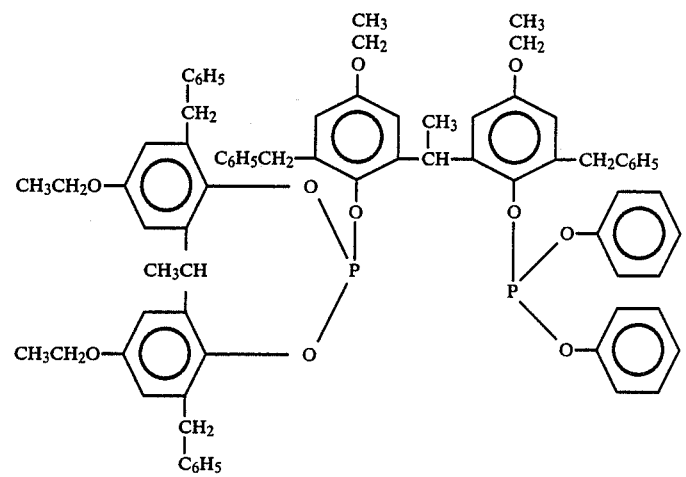
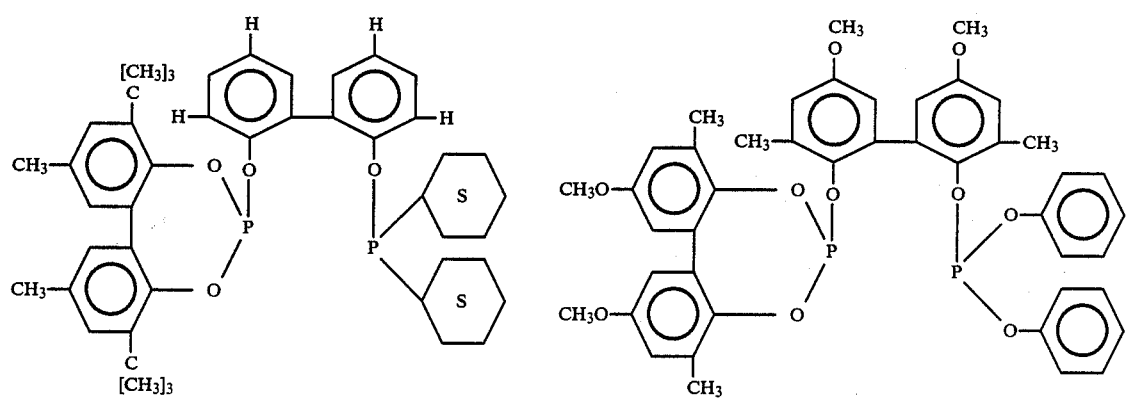
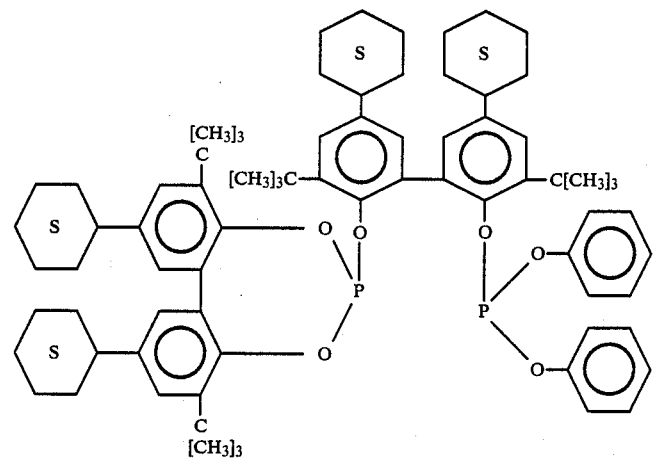

-continued
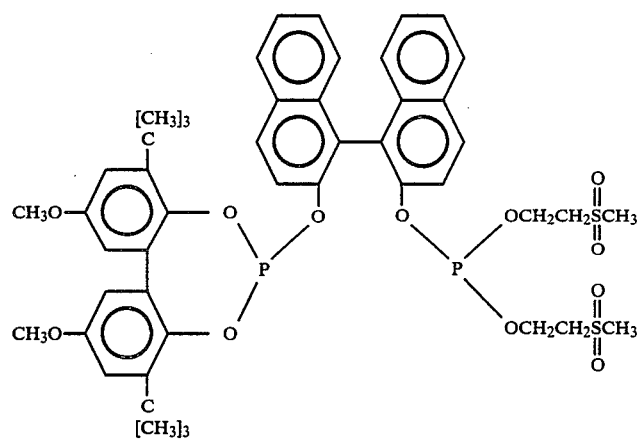
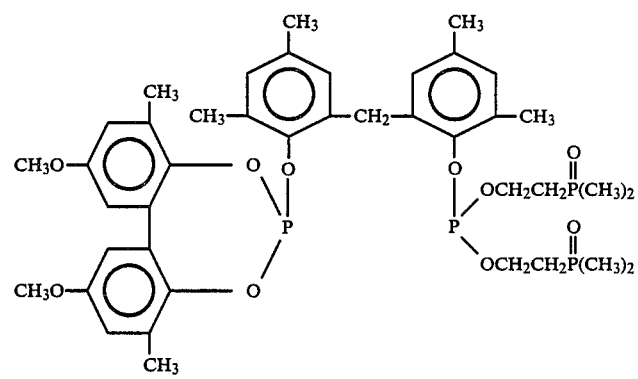
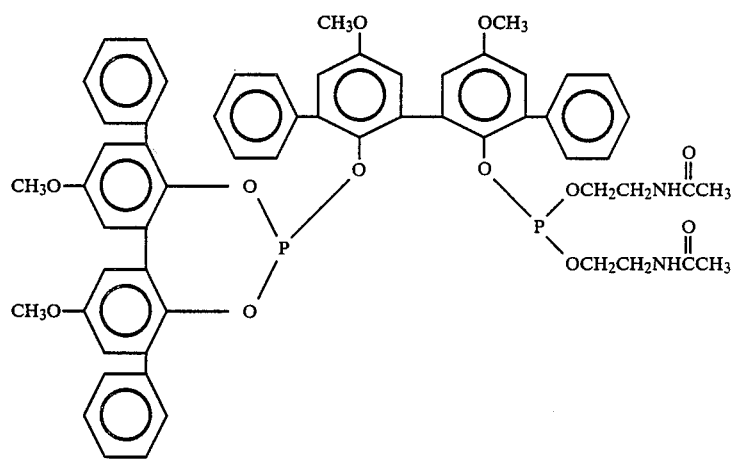
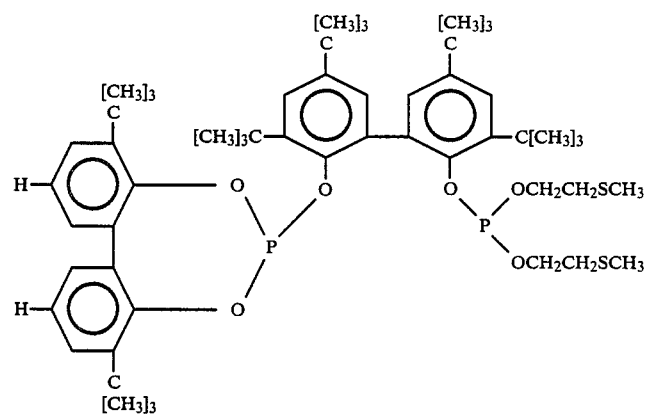

-continued
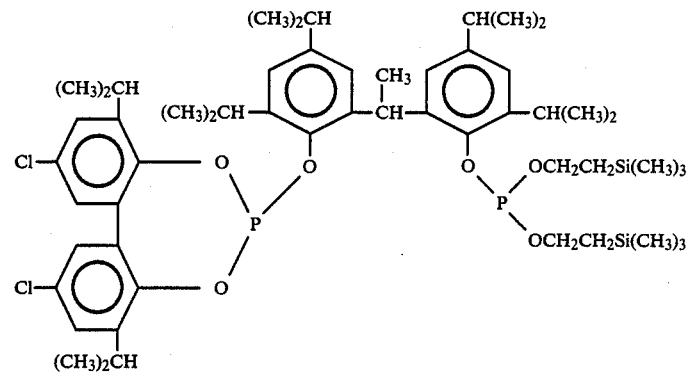
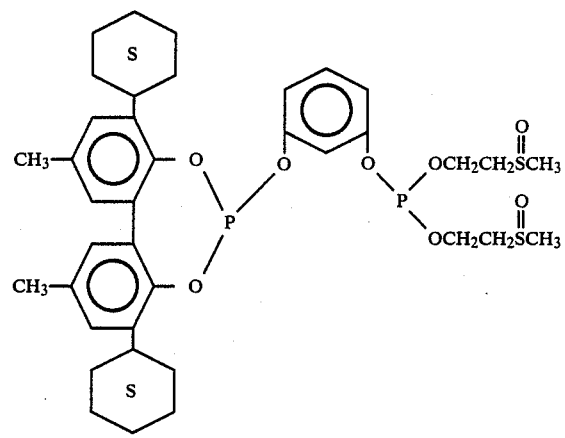
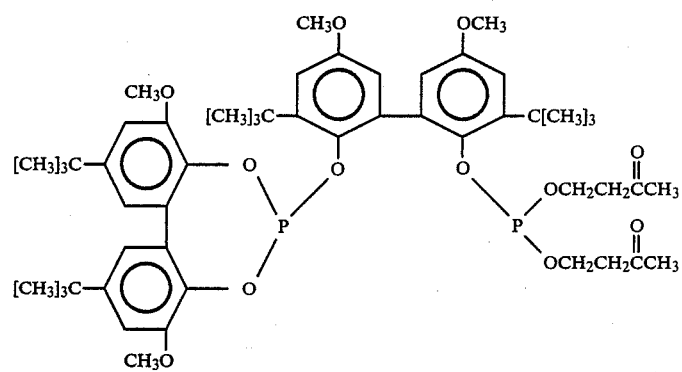
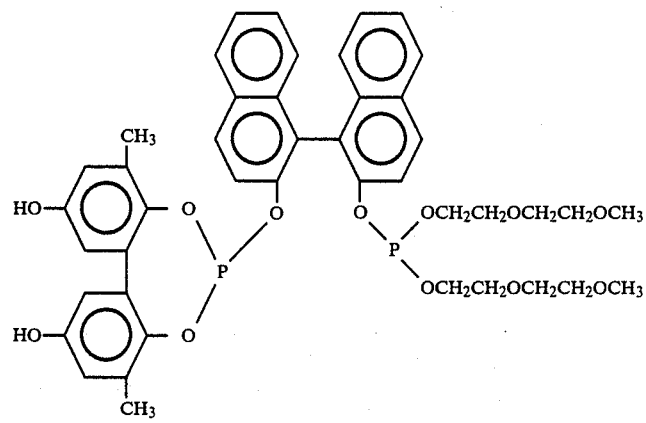

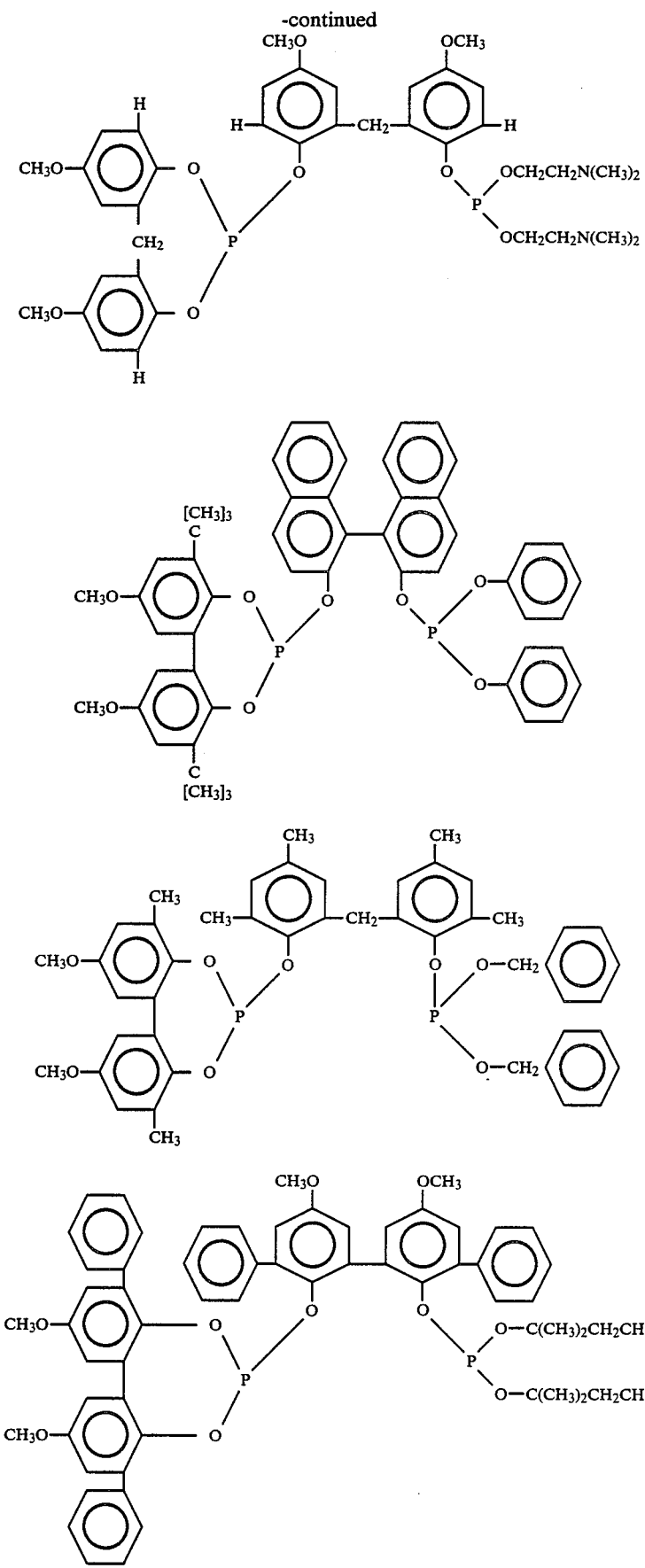

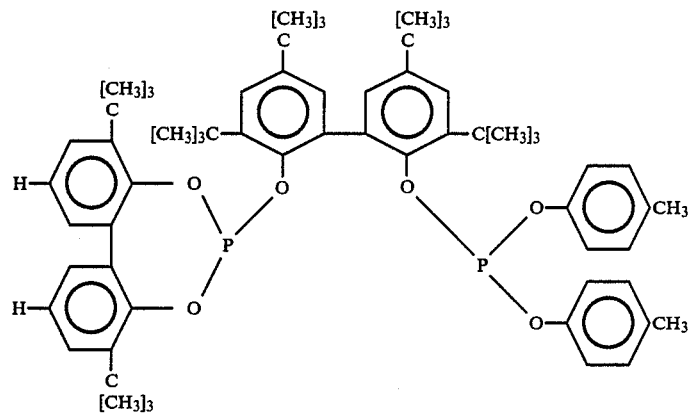
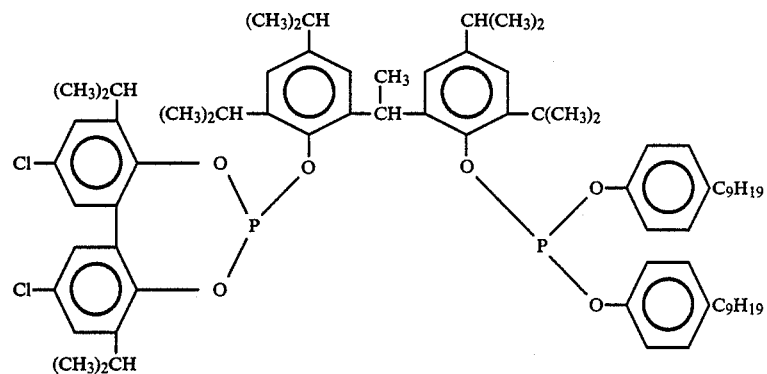
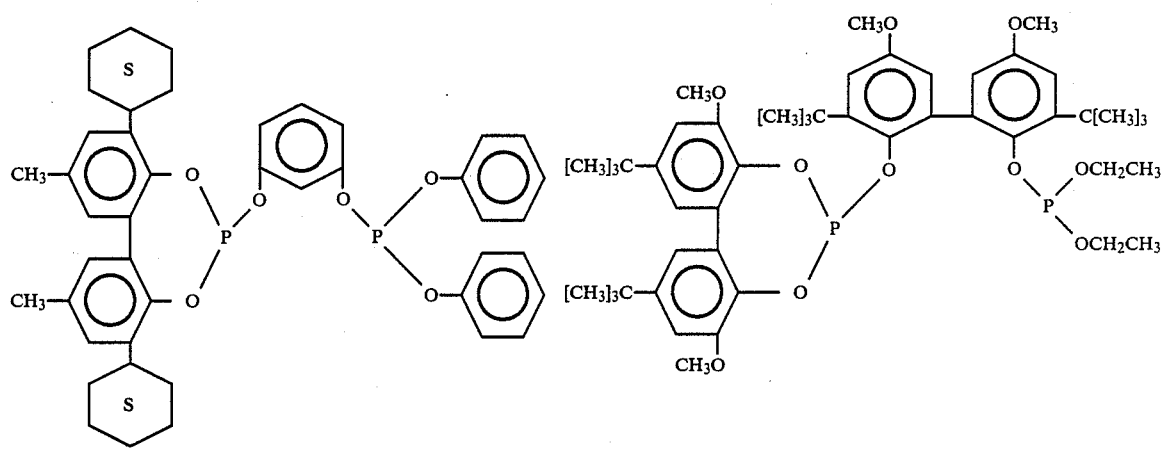
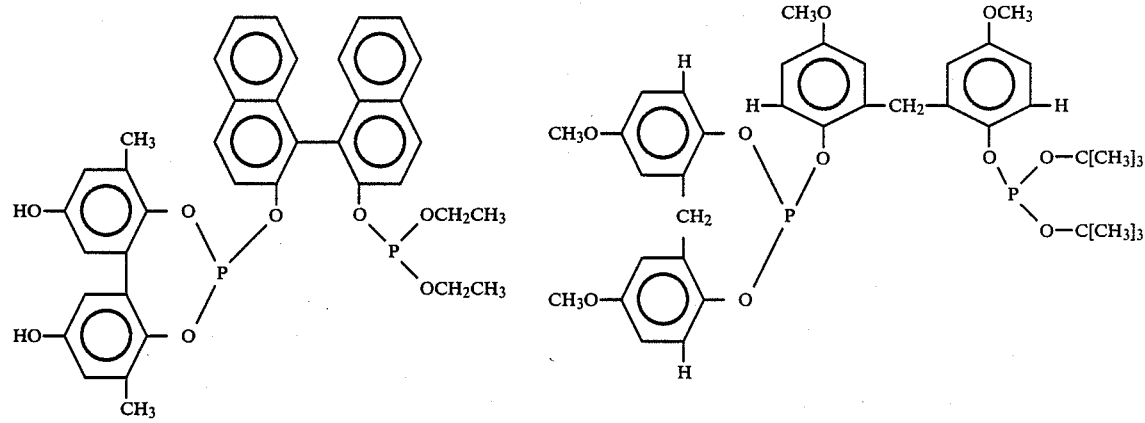

51 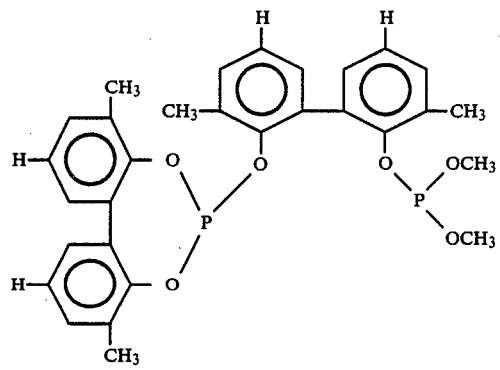
52 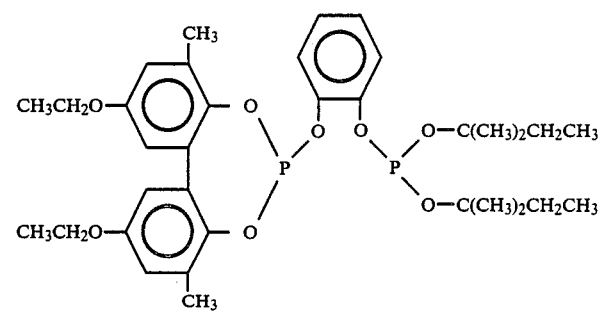
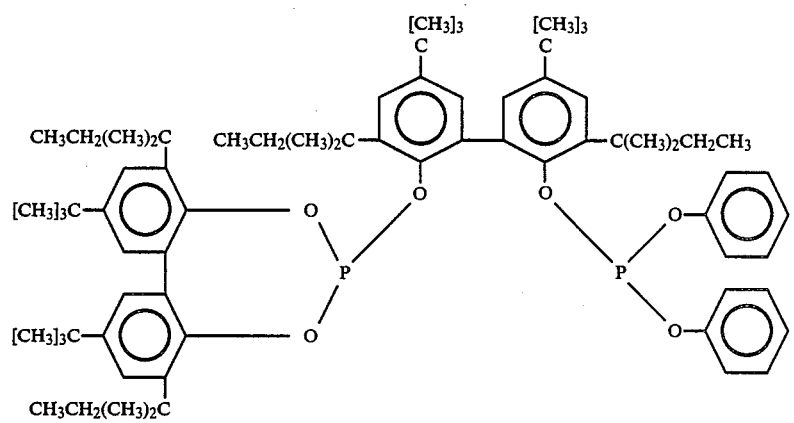
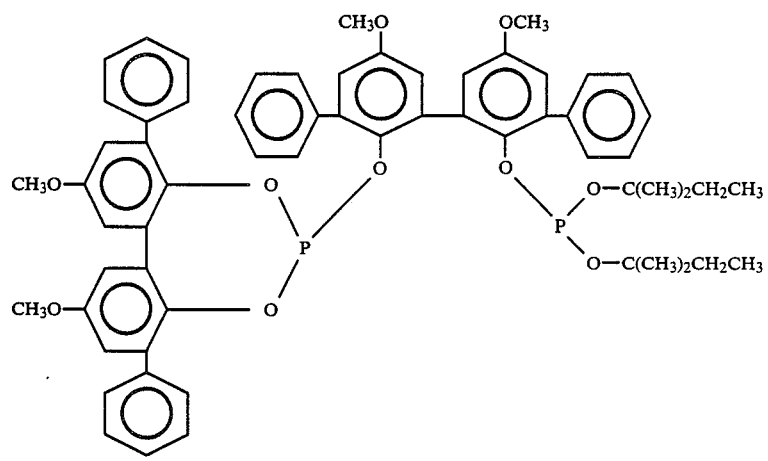
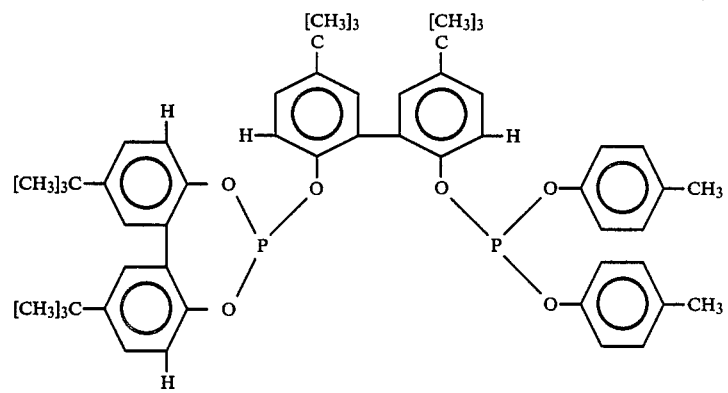

-continued
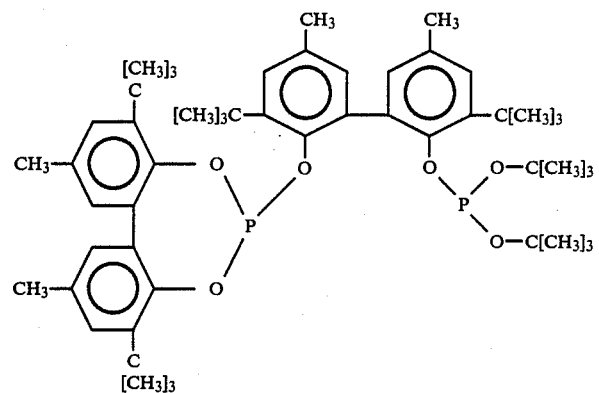
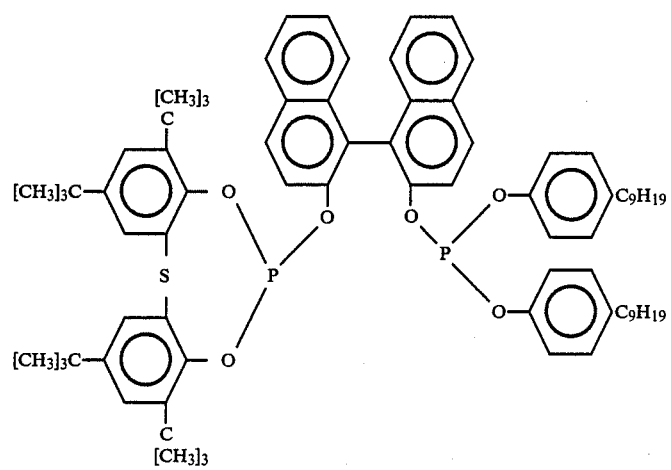
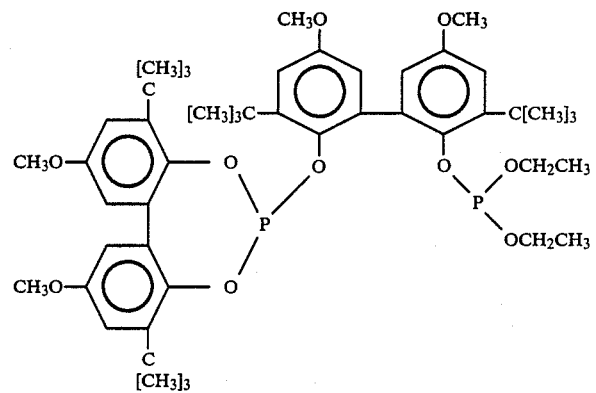

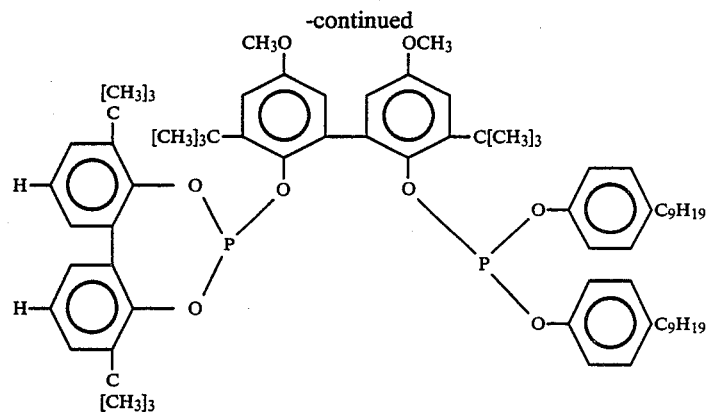
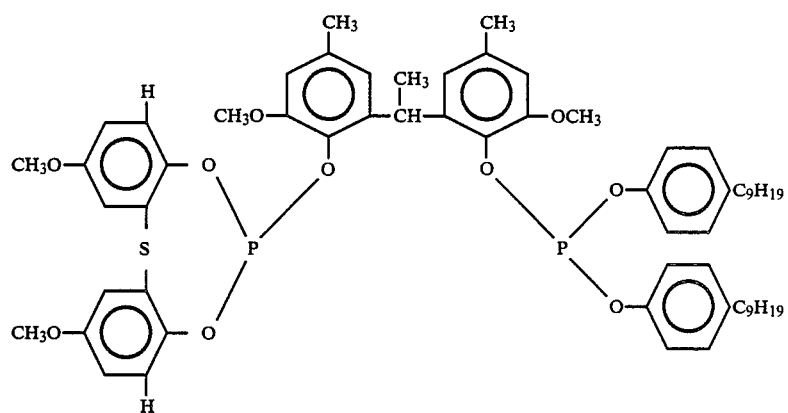
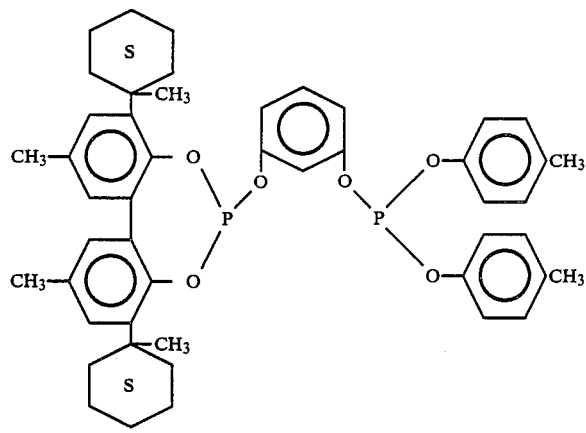
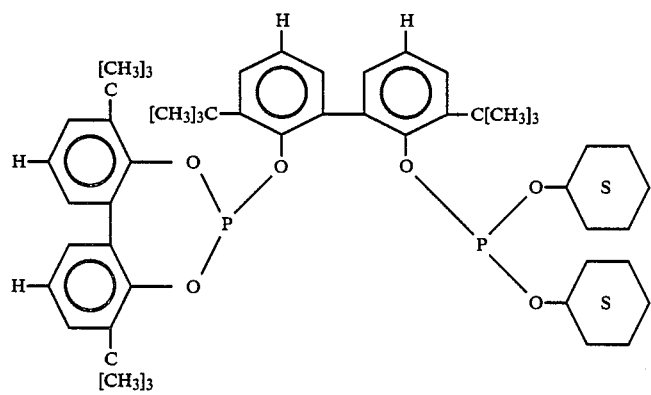

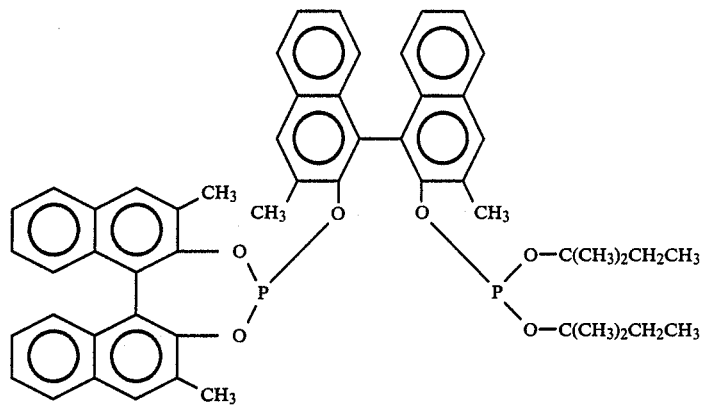
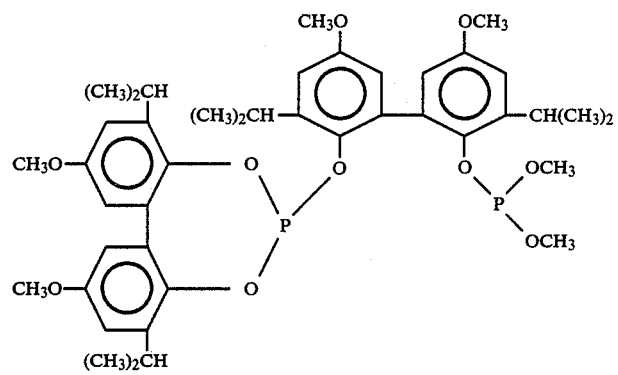
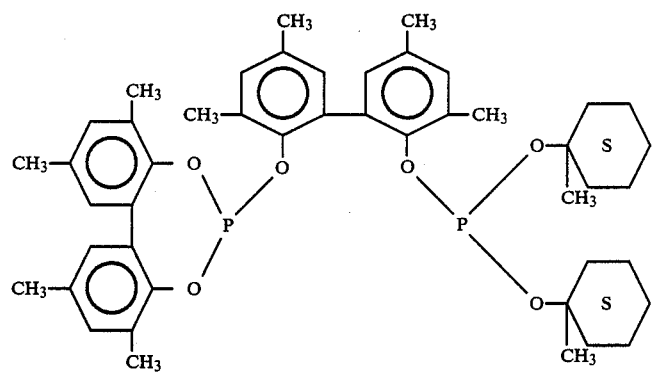
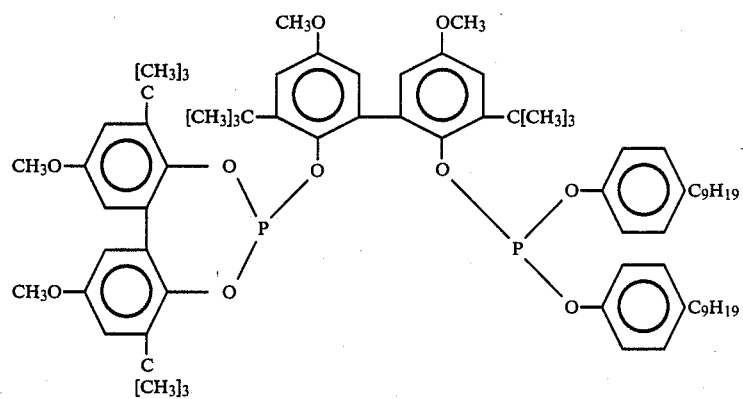

-continued
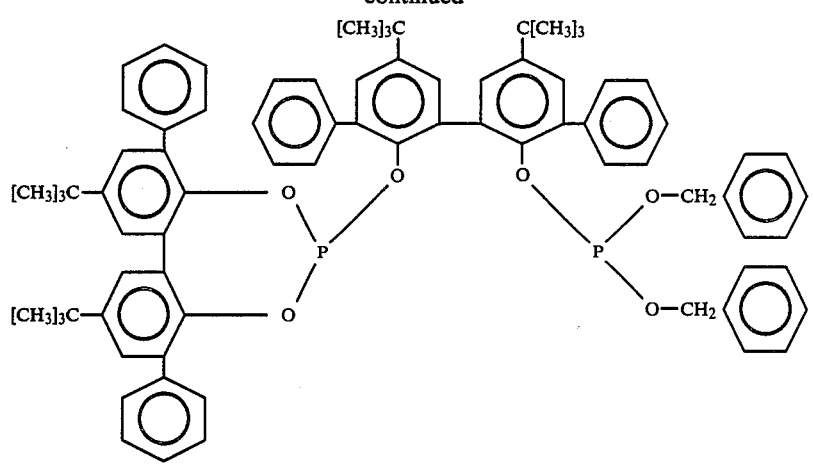
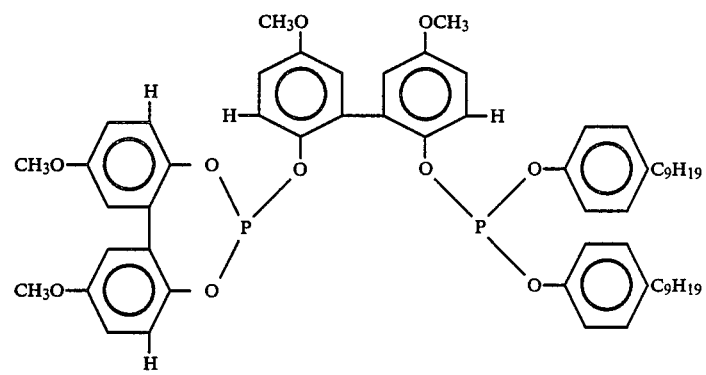
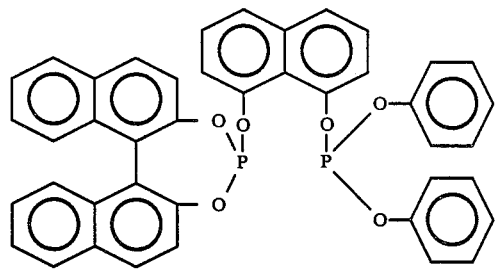
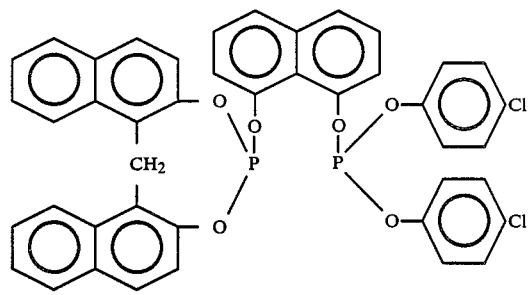
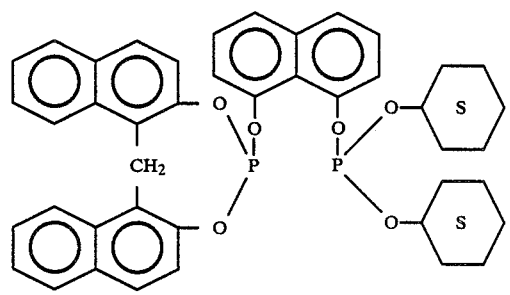
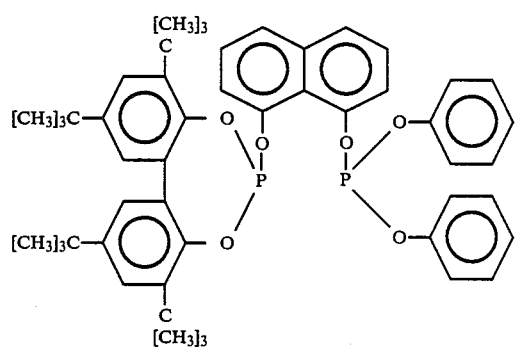

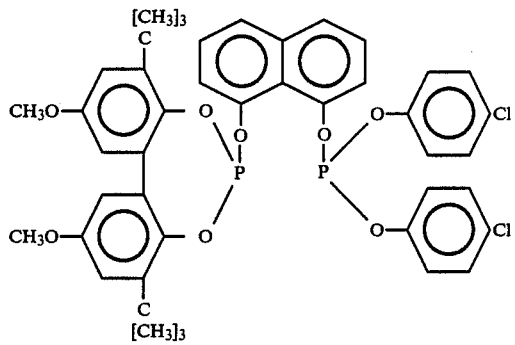
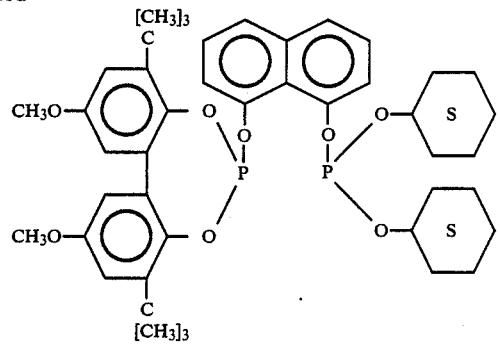
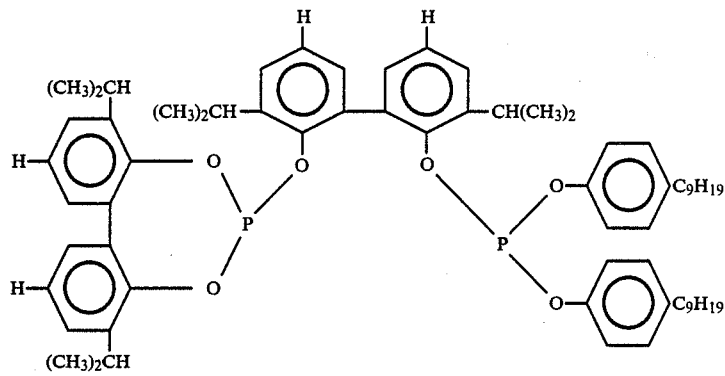
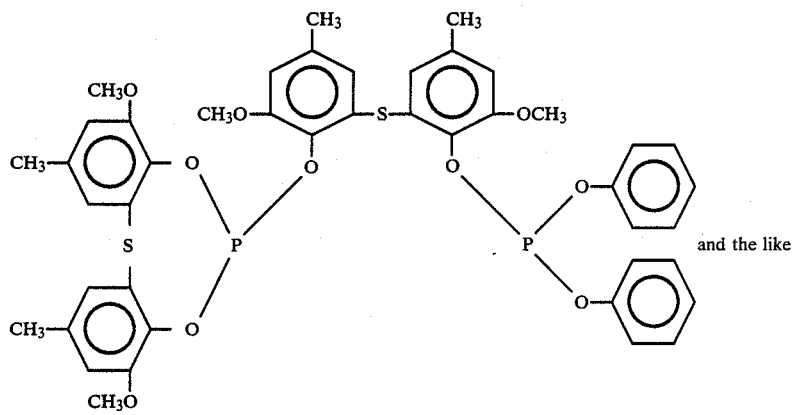

and the like

The bis-phosphite ligands employable in this invention can be readily and easily prepared via a series of conventional phosphorus halide-alcohol condensation reactions. Such types of condensation reactions and the manner in which they may be conducted are well known in the art. For instance a simple method for preparing such ligands may comprise (a) reacting a corresponding organic diphenolic compound with phosphorus trichloride to from the corresponding organic phosphorochloridite intermediate, (b) reacting said intermediate with a diol (corresponding to W in the above formulas) to form the corresponding hydroxy substituted diorganophosphite intermediate, (c) reacting said diorganophosphite intermediate with phosphorus trichloride to from the corresponding phosphorodichloridite intermediate and (d) reacting said dichloridite with two moles of a corresponding mono-ol to arrive at the corresponding desired bis-phosphite ligand. Said condensation reactions are preferably carried out in the presence of a solvent, e,g. toluene, and an HCl acceptor, e.g. an amine, and may be carried out in a single-pot synthesis, if desired.

The bis-phosphite ligands of this invention are unique compounds that in general possess higher molecular weight and lower volatility properties than heretofore conventional type phosphorus ligands and have been found to be especially useful ligands in the homogeneous catalyzed hydroformylation of olefinically unsaturated compounds. Such is indeed surprising since due to their high molecular weight one might expect such ligands to have low solubility in the reaction media of such hydroformylation processes. Further, the use of the bis-phosphite ligands can provide an excellent means for controlling product selectivity in hydroformylation reactions. For instance, the bis-phosphites have been found to be very effective ligands when oxygenated products, e.g. aldehydes, having very high nornmal to iso (branched) product ratios are desired.

Without wishing to be bound to any exact theory or mechanistic discourse, it appears that it is the special structural features of the bis-phosphite ligands in Formulas IV through XII above which make them unique hydroformylation catalysts promoters capable of providing extremely high normal to iso (branched) aldehyde product ratios. These features appear to include the steric size of the two phosphorus groups of the bis-phosphite as well as the steric size of the bridging group W and the relationship of the two phosphorous groups to each other. As noted above the more preferred bis-phosphite ligands include those wherein W is selected from the group consisting of 1,8-naphthylene, 2,3-naphthylene and 1,2-naphthylene and those wherein the two phenylene radicals or two naphthylene radicals of W linked by the bridging group represented by —(Q-)$_n$— are bonded through their ortho positions in relation to the oxygen atoms that connect the two phenylene or two naphthylene radicals to their respective phosphorus atoms (or groups). It has been surprisingly discovered that such bis-phosphites containing the two phosphorus atoms (or groups) in such a relationship have the ability of forming chelate complexes with transition metals e.g. rhodium. Such 9 or 10 membered chelate complexes are a completely unique phenomenon in the art and are believed to be the primary reason responsible for the very high reaction rates and very high normal:iso aldehyde product selectivities obtainable with the use of such bis-phosphites in the hydroformylation of both alpha olefins and internal olefins. Typical prior art metal chelates comprise only 4 through 7, and most preferably 5 and 6 membered chelate complexes.

For example, infra red spectroscopic and X-ray crystallographic data of a rhodium complex of revealed that the ligand prefers to doubly coordinate the rhodium and form chelate complexes e.g. as seen by the formula:

ligand itself as well as the size of the other substituent groups in the bis-phosphite molecule are considered important factors with regard to the chelateability of the bis-phosphite ligands. Too much steric hindrance may well effect the ability of the bis-phosphite to chelate, while not enough steric hindrance may cause the bis-phosphite to chelate too strongly. For example, it is considered that all of the bis-phosphite ligands of Formulas IV through XII above are capable of producing chelated rhodium complexes and very high normal to iso aldehyde product ratios via hydroformylation. However, such does not appear to be possible e.g. W is too sterically contained (rigid) to form a metal chelate complex as in the case e.g. when W represents a 1,1'-biphenyl-4'4-diyl radical or the like.

It is, of course, to be understood that the possible inability of other bis-phosphites to form chelate metal complexes in no way should be considered to detract from the novelty or usefulness of such bis-phosphites as ligand promoters in e.g. hydroformylation, but only that they are not on a par with regard to achieving the very high normal to iso aldehyde product ratios that are possible with the bis-phosphites which do have such chelateability properties.

As noted above the bis-phosphite ligands defined above are employed in this invention as both the phosphorus ligand of the Group VIII transition metal complex catalyst, as well as, the free phosphorus ligand that is preferably present in the reaction medium of the process of this invention. In addition, it is to be understood that while the phosphorus ligand of the Group VIII transition metal-bis-phosphite complex catalyst and excess free phosphorus ligand preferably present in a given process of this invention are normally the same type of bis-phosphite ligand, different types of bis-phosphite ligands, as well as, mixtures of two or more different bis-phosphite ligands may be employed for each purpose in any given process, if desired.

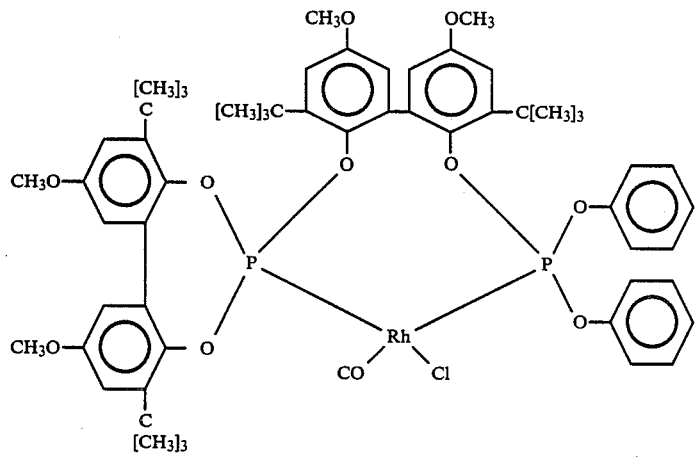

It is believed that the high normal to iso product selectives obtained with such chelateable ligands is a reflection of this cis chelation ability of the ligand which appears to create a steric environment around the rhodium favoring the formation of linear hydroformylation products. Moreover, the overall size of the As in the case of prior art Group VIII transition metal-phosphorus complex catalysts, the Group VIII transition metal-bis-phosphite complex catalysts of this invention may be formed by methods known in the art. For instance, preformed Group VIII transition metal hydrido-carbonyl (bis-phosphite) catalysts may possibly be prepared and introduced into the reaction medium of a hydroformylation process. More preferably, the Group VIII transition metal-bis-phosphite complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$ and the like may be introduced into the reaction medium along with the bis-phosphite ligand for the in situ formation of the active catalyst. In a preferred embodiment rhodium dicarbonyl acetylacetonate is employed as a rhodium precursor and reacted in the presence of a solvent with the bis-phosphite to form a catalytic rhodium-bis-phosphite complex precursor which is introduced into the reactor along with excess free bis-phosphite ligand for the in situ formation of the active catalyst. In any event, it is sufficient for the purpose of this invention to understand that carbon monoxide, hydrogen and bis-phosphite are all ligands that are capable of being complexed with the Group VIII transition metal, e.g. rhodium and that an active Group VIII transition metal-bis-phosphite catalyst is present in the reaction medium under the conditions of the carbonylation and more preferably hydroformylation process.

Accordingly, the Group VIII transition metal-bis-phosphite complex catalysts of this invention may be defined as consisting essentially of a Group VIII transition metal complexed with carbon monoxide and a bis-phosphite ligand, said ligand being bonded (complexed) to the metal, e.g. rhodium in a chelated and/or non-chelated fashion. Moreover, it is to be understood that the catalyst terminology "consisting essentially of" is not meant to exclude, but rather can include hydrogen complexed with the metal particularly in the case of rhodium catalyzed hydroformylation, in addition to carbon monoxide and the bis-phosphite ligand. Further, as noted above such terminology is also not meant to exclude the possibility of other organic ligands and/or anions that might also be complexed with the metal. However, such catalyst terminology preferably is meant to exclude other materials in amounts which unduly adversely poison or unduly deactivate the catalyst and thus rhodium most desirably is free of contaminants such as rhodium bound halogen e.g. chlorine, and the like. As noted, the hydrogen and/or carbonyl ligands of an active rhodium-bis-phosphite complex catalyst may be present as a result of being ligands bound to a precursor catalyst and/or as a result of in situ formation e.g. due to the hydrogen and carbon monoxide gases employed in a hydroformylation process.

Moreover, like prior art Group VIII transition metal phosphorus ligand complex catalysts it is clear that the amount of complex catalyst present in the reaction medium of a given process of this invention need only be that minimum amount necessary to provide the given Group VIII transition metal concentration desired to be employed and which will furnish the basis for at least that catalytic amount of Grouup VIII transition metal necessary to catalyze the particular carbonylation process desired. In general, Group VIII transition metal concentrations in the range of from about 10 ppm to about 1000 ppm, calculated as free metal, should be sufficient for most carbonylation processes. Moreover, in the rhodium catalyzed hydroformylation processes of this invention, it is generally preferred to employ from about 10 to 500 ppm of rhodium and more preferably from 25 to 350 ppm of rhodium, calculated as free metal.

The olefinic starting material reactants encompassed by the processes of this invention can be terminally or internally unsaturated and be of straight chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethyl-hexene, styrene, 3-phenyl-1-propene, 1,4-hexadiene, 1,7 octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, and the like. Of course, it is understood that mixtures of different olefinic starting materials can be employed, if desired, by the hydroformylation process of the subject invention. More preferably the subject invention is especially useful for the production of aldehydes, by hydroformylating alpha olefins containing from 2 to 20 carbon atoms and internal olefins containing from 4 to 20 carbon atoms as well as starting material mixtures of such alpha olefins and internal olefins.

The carbonylation and preferably hydroformylation process of this invention is also preferably conducted in the presence of an organic solvent for the Group VIII transition metal-bis-phosphite complex catalyst. Any suitable solvent which does not unduly adversely interfere with the intended carbonylation process can be employed and such solvents may include those heretofore commonly employed in known Group VIII transition metal catalyzed processes. By way of illustration suitable solvents for rhodium catalyzed hydroformylation processes include those disclosed e.g. in U.S. Pat. Nos. 3,527,809 and 4,148,830. Of course, mixtures of one more different solvents may be employed if desired. In general, in rhodium catalyzed hydroformylation it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ, if desired, any suitable solvent at the start up of a continuous process (aldehyde compounds corresponding to the desired aldehyde products being preferred), the primary solvent will normally eventually comprise both aldehyde products and higher boiling aldehyde liquid condensation by-products due to the nature of such continuous processes. Such aldehyde condensation by-products can also be preformed if desired and used accordingly. Moreover, such higher boiling aldehyde condensation by-products and methods for their preparation are more fully described in U.S. Pat. Nos. 4,148,830 and 4,247,486. Of course, it is obvious that the amount of solvent employed is not critical to the subject invention and need only be that amount sufficient to provide the reaction medium with the particular Group VIII transition metal concentration desired for a given process. In general, the amount of solvent when employed may range from about 5 percent by weight up to about 95 percent by weight or more based on the total weight of the reaction medium.

It is further generally preferred to carry out the carbonylation and especially the hydroformylation process of this invention in a continuous manner. Such types of continuous processes are well known in the art and may involve e.g. hydroformylating the olefinic starting material with carbon monoxide and hydrogen in a liquid homogeneous reaction medium comprising a solvent, the Group VIII transition metal-bis-phosphite catalyst, and free bis-phosphite ligand; supplying make-up quantities of the olefinic starting material, carbon monoxide and hydrogen to the reaction medium; maintaining reaction temperature and pressure conditions favorable to the hydroformylation of the olefinic starting material; and recovering the desired aldehyde hydroformylation product in any conventional manner desired. While the continuous process can be carried out in a single pass mode, i.e. wherein a vaporous mixture comprising unreacted olefinic starting material and vaporized aldehyde product is removed from the liquid reaction medium from whence the aldehyde product is recovered and make-up olefinic starting material, carbon monoxide and hydrogen are supplied to the liquid reaction medium for the next single pass through without recycling the unreacted olefinic starting material, it is generally desirable to employ a continuous process that involves either a liquid and/or gas recycle procedure. Such types of recycle procedures are well known in the art and may involve the liquid recycling of the Group VIII transition metal-bis-phosphite complex catalyst solution separated from the desired aldehyde reaction product, such as disclosed e.g. in U.S. Pat. No. 4,148,830 or a gas recycle procedure such as disclosed e.g. in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

The desired aldehyde product may be recovered in any conventional manner such as described, e.g. in U.S. Pat. Nos. 4,148,830 and 4,247,486. For instance, in a continuous liquid catalyst recycle process the portion of the liquid reaction solution (containing aldehyde product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction solution may then be recycled back to the reactor as may if desired any other volatile materials, e.g. unreacted olefin, together with any hydrogen and carbon monoxide dissolved in the liquid reaction solution after separation thereof from the condensed aldehyde product, e.g. by distillation in any conventional manner. In general, it is preferred to separate the desired aldehyde product from the rhodium catalyst containing product solution under reduced pressure and at low temperatures such as below 150° C. and more preferably below 130° C.

As noted above, the carbonylation process and especially the hydroformylation process of this invention is preferably carried out in the presence of free bis-phosphite ligand, i.e. ligand that is not complexed with the Group VIII transition metal of the metal complex catalyst employed. Thus the free bis-phosphite ligand may correspond to any of the above defined bis-phosphite ligands discussed above. However, while it is preferred to employ a free bis-phosphite ligand that is the same as the bis-phosphite ligand of the Group VIII transition metal-bis-phosphite complex catalyst such ligands need not be the same in a given process, but can be different if desired. While the carbonylation and preferably hydroformylation process of this invention may be carried out in any excess amount of free bis-phosphite ligand desired, e.g. at least one mole of free bis-phosphite ligand per mole of Group VIII transition metal present in the reaction medium, the employment of free bis-phosphite ligand may not be absolutely necessary. Accordingly, in general amounts of bis-phosphite ligand of from about 4 to about 100, or higher if desired, and preferably from about 3 to about 50, moles per mole of Group VIII transition metal (e.g. rhodium) present in the reaction medium should be suitable for most purposes, particularly with regard to rhodium catalyzed hydroformylation; said amounts of bis-phosphite ligand employed being the sum of both the amount of bis-phosphite that is bound (complexed) to the Group VIII transition metal present and the amount of free (non-complexed) bis-phosphite ligand present. Of course, if desired, make-up bis-phosphite ligand can be supplied to the reaction medium of the hydroformylation process, at any time and in any suitable manner, to maintain a predetermined level of free ligand in the reaction medium.

The ability to carry out the process of this invention in the presence of free bis-phosphite ligand is an important beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

The reaction conditions for effecting a carbonylation and more preferably a hydroformylation process of this invention may be those heretofore conventionally used and may comprise a reaction temperature of from about 45° C. to about 200° C. and pressures ranging from about 1 to 10,000 psia. While the preferred carbonylation process is the hydroformylation of olefinically unsaturated compounds and more preferably olefinic hydrocarbons, with carbon monoxide and hydrogen to produce aldehydes, it is to be understood that the Group VIII transition metal-bis-phosphite complexes of this invention may be employed as catalysts in any other type of prior art carbonylation process to obtain good results. Moreover, while such other prior carbonylation art processes may be performed under their usual conditions, in general it is believed that they may be performed at lower temperatures than normally preferred due to the Group VIII transition metal-bis-phosphite complex catalysts of this invention.

As noted the more preferred process of this invention involves the production of aldehydes via hydroformylation of an olefinic unsaturated compound with carbon monoxide and hydrogen in the presence of a Group VIII transition metal-bis-phosphite complex catalyst and free bis-phosphite ligand, especially a rhodium-bis-phosphite complex catalyst.

The bis-phosphite ligands employable herein provide an excellent means for controlling product selectivity, and more preferably obtaining very high linear (normal) aldehyde product selectivity, in hydroformylation reactions. Indeed preferred bis-phosphite ligands employable herein may provide aldehyde hydroformylation products from sterically unhindered alpha olefins having high normal to branched isomer product ratios that are as comparable, if not superior, in their normal aldehyde product content than heretofore comparatively obtainable by most any prior art phosphorus ligands. More especially preferred bis-phosphite ligands employable herein have been found to provide aldehyde hydroformylation products from internal olefins that have such high linear (normal) to branched chain (isomer) product ratios, that they are unprecedented in the art. Moreover the ability to hydroformylate both alpha and internal olefins with ease allows one to hydroformylate both types of olefins (e.g. mixtures of butene-1 and butene-2) concurrently with comparable facility from the same starting material mixture. Such is highly beneficial to the art since such mixed alpha olefin and internal olefin starting materials are readily available and are the most economical olefin feedstocks. Moreover, the versatility of the bis-phosphite ligands employable herein lend themselves readily to the continuous hydroformylation of both alpha-olefins and internal olefins wherein different reactors in series may be employed. Such ability not only provides one with the processing latitude of further hydroformylating in the second reactor any unreacted olefin passed to it from the first reactor but also allows one, if desired, to optimize the reaction conditions for hydroformylation of e.g. the alpha-olefin in the first reactor, while also optimizing the reaction conditions for the hydroformylation of e.g. the internal olefin in the second reactor.

Of course, it is to be understood that while the optimization of the reaction conditions necessary to achieve the best results and efficiency desired are dependent upon one's experience in the utilization of the subject hydroformylation invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

For instance, the total gas pressure of hydrogen, carbon monoxide and olefinic unsaturated starting compound of the hydroformylation process of this invention may range from about 1 to about 10,000 psia. More preferably, however, in the hydroformylation of olefins to produce aldehydes it is preferred that the process be operated at a total gas pressure of hydrogen, carbon monoxide and olefinic unsaturated starting compound of less than about 1500 psia. and more preferably less than about 500 psia. The minimum total pressure of the reactants is not particularly critical and is limited predominately only by the amount of reactants necessary to obtain a desired rate of reaction. More specifically the carbon monoxide partial pressure of the hydroformylation process of this invention is preferably from about 1 to about 120 psia. and more preferably from about 3 to about 90 psia, while the hydrogen partial pressure is preferably about 15 to about 160 psia and more preferably from about 30 to about 100 psia. In general $H_2:CO$ molar ratio of gaseous hydrogen to carbon monoxide may range from about 1:10 to 100:1 or higher, the more preferred hydrogen to carbon monoxide molar ratio being from about 1:1 to about 10:1.

Further as noted above the hydroformylation process of this invention may be conducted at a reaction temperature from about 45° C. to about 200° C. The preferred reaction temperature employed in a given process will of course be dependent upon the particular olefinic starting material and metal catalyst employed as well as the efficiency desired. In general, hydroformylations at reaction temperatures of about 50° C. to about 120° C. are preferred for all types of olefinic starting materials. More preferably, alpha-olefins can be effectively hydroformylated at a temperature of from about 60° C. to about 110° C. while even less reactive olefins than conventional alpha-olefins such as isobutylene and internal olefins as well as mixtures of alpha-olefins and internal olefins are effectively and preferably hydroformylated at a temperature of from about 70° C. to about 120° C. Indeed in the rhodium-catalyzed hydroformylation process of this invention no substantial benefit is seen in operating at reaction temperatures much above 120° C. and such is considered to be less desirable.

As outlined herein the carbonylation and more preferably hydroformylation process of this invention can be carried out in either the liquid or gaseous state and involve a continuous liquid or gas recycle system or combination of such systems. Preferably the rhodium catalyzed hydroformylation of this invention involves a continuous homogeneous catalysis process wherein the hydroformylation is carried out in the presence of both free bis-phosphite ligand and any suitable conventional solvent as further outlined herein.

Thus in general the use of the bis-phosphite ligands of this invention are unique in that they provide very good catalytically active and stable rhodium catalysts for the production of aldehydes which most preferably have very high straight-chain (normal) to branched-chain (iso) product ratios via the hydroformylation of olefins, especially internal olefins. Moreover the low volatility possessed by such high molecular weight bis-phosphite ligands renders them especially suitable for use in hydroformylating higher olefins, e.g. olefins of four or more carbon atoms. For example volatility is related to molecular weight and is inversely proportional to molecular weight within a homologous series. Accordingly it is generally desirable to employ a phosphorus ligand whose molecular weight exceeds that of the higher boiling aldehyde by-product trimer corresponding to the aldehyde being produced in the hydroformylation process in order to avoid or at least minimize possible ligand loss during removal via distillation of the aldehyde product and/or higher boiling aldehyde condensation by products, when desired, from the reaction system. Thus for instance, since the molecular weight of valeraldehyde trimer is about 250 ($C_{15}H_{30}O_3$) and all the bis-phosphites of this invention will exceed 250 in molecular weight, there should not be any unduly detrimental loss of the bis-phosphite ligand during such higher product aldehyde and/or such higher boiling aldehyde by-product removal from the reaction system.

Moreover, in a continuous liquid rhodium catalyzed recycle process it is possible that an undesirable hydroxy alkyl phosphine acid by-product may result due to reaction of the bis-phosphite ligand and aldehyde product over the course of such a continuous process causing a loss of ligand concentration. Such an acid is often insoluble in the general liquid hydroformylation reaction medium and can lead to precipitation of an undesirable gellatinous by-product and may also promote the autocatalytic formation of itself. However if such a problem does occur with the use of the bis-phosphite ligands of this invention it is considered that it may be effectively and preferably controlled by passing the liquid reaction effluent stream of a continuous liquid recycle process either prior to or more preferably after separation of the aldehyde product therefrom through any suitable weakly basic anion exchange resin, such as a bed of amine-Amberlyst* resin, e.g. Amberlyst* A-21, and the like, to remove some or all of the undesirable hydroxy alkyl phosphonic acid by-product that might be present in the liquid catalyst containing stream prior to its reincorporation into the hydroformylation reactor. Of course if desired, more than one such basic anion exchange resin bed, e.g. a series of such beds, may be employed and any such bed may be easily removed and/or replaced as required or desired. Alternatively if desired, any part or all of the hydroxy alkyl phosphonic acid contaminated catalyst recycle stream may be periodically removed from the continuous recycle operation and the contaminated liquid so removed treated in the same fashion as outlined above, to eliminate or reduce the amount of hydroxy alkyl phosphonic acid contained therein prior to reusing the catalyst containing liquid in the hydroformylation process. Likewise, any other suitable method for removing such hydroxy alkyl phosphonic acid by-product from the hydroformylation process of this invention may be employed herein if desired such as by extraction of the acid with a weak base, e.g. sodium bicarbonate.

A further aspect of this invention can be described as a catalyst precursor composition consisting essentially of a solubilized Group VIII transition metal-bis-phosphite complex precursor catalyst, an organic solvent and free bis-phosphite ligand. Such precursor compositions may be prepared by forming a solution of a Group VIII transition metal starting material, such as a metal oxide, hydride, carbonyl or salt e.g. a nitrate, which may or may not be in complex combination with a bis-phosphite ligand, an organic solvent and a free bis-phosphite ligand as defined herein. Any suitable Group VIII transition metal starting material may be employed e.g. rhodium dicarbonyl acetylacetonate, $Rh_2O_3$, $Rh_4(CO)_{12}$, $Rh_6(CO)_{16}$, $Rh(NO_3)_3$, bis-phosphite rhodium carbonyl hydrides, iridium carbonyl, bis-phosphite iridium carbonyl hydrides, osmium halide, chloroosmic acid, osmium carbonyls, palladium hydride, palladous halides, platinic acid, platinous halides, ruthenium carbonyls, as well as other salts of other Group VIII transition metals and carboxylates of $C_2$–$C_{16}$ acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course any suitable solvent may be employed such as e.g. those employable in the carbonylation process desired to be carried out. The desired carbonylation process may of course also dictate the various amounts of metal, solvent and ligand present in the precursor solution. Carbonyl and bis-phosphite ligands if not already complexed with the initial Group VIII transition metal may be complexed to the metal either prior to or in situ during the carbonylation process. By way of illustration, since the preferred Group VIII transition metal is rhodium and since the preferred carbonylation process is hydroformylation, the preferred catalyst precursor composition of this invention consists essentially of a solubilized rhodium carbonyl bis-phosphite complex precursor catalyst, an organic solvent and free bis-phosphite ligand prepared by forming a solution of rhodium dicarbonyl acetylacetonate, an organic solvent and a bis-phosphite ligand as defined herein. The bis-phosphite readily replaces one of the dicarbonyl ligands of the rhodium-acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium bis-phosphite complex precursor are soluble can be employed. Accordingly, the amounts of rhodium complex catalyst precursor, organic solvent and bis-phosphite, as well as their preferred embodiments present in such catalyst precursor compositions may obviously correspond to those amounts employable in the hydroformylation process of this invention and which have already been discussed herein. Experience has shown that the acetylacetonate ligand of the precursor catalyst is replaced after the hydroformylation process has begun with a different ligand, e.g. hydrogen, carbon monoxide or bis-phosphite ligand, to form the active rhodium complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions thus provides a simple economical and efficient method for handling the rhodium precursor metal and hydroformylation start-up.

Finally, the aldehyde products of the hydroformylation process of this invention have a wide range of utility that is well known and documented in the prior art e.g. they are especially useful as starting materials for the production of alcohols and acids.

The following examples are illustrative of the present invention and are not to be regarded as limitative. It is to be understood that all of the parts, percentages and proportions referred to herein and in the appended claims are by weight unless otherwise indicated. In the formulas of this specification a tertiary butyl radical is represented by —C[CH3]3 or t-Bu; while —C6H5 represents a phenyl radical, OMe represents a methoxy radical and a nonyl or [—C9H19] radical represents branched mixed nonyl radicals. Sometimes —H is used to represent the absence of any substituent other than hydrogen in that particular position of the formula.

EXAMPLE 1

A series of various rhodium complex catalyst precursor solutions consisting essentially of the solubilized reaction product of rhodium dicarbonyl acetylacetonate and various bis-phosphite ligands were prepared and employed to hydroformylate butene-1 into C5 aldehydes in the following manner.

Rhodium dicarbonyl acetylacetonate was mixed at ambient temperature with various bis-phosphite ligands having the formula:

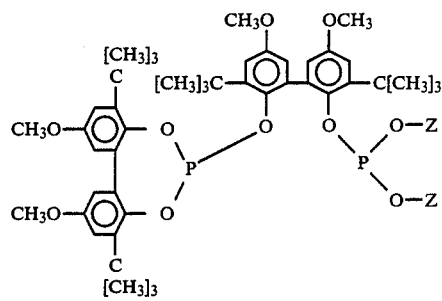

wherein each Z represents a radical as shown in TABLE 1 below, and a solvent to produce the various rhodium catalytic precursor solutions containing the amounts of rhodium and ligands shown in Table 1 below.

Each rhodium catalytic precursor solution so prepared was then employed to hydroformylate butene-1 in a magnetically stirred, 100 mL capacity, stainless steel autoclave which was attached to a gas manifold for introducing gases to the desired partial pressure. The autoclave was also equipped with a pressure calibrator for determining reaction pressure to ±0.01 psia. and a platinum resistance thermometer for determining reactor solution temperatures to ±0.1° C. The reactor was heated externally by two 300 watt heating bands. The reactor solution temperature was controlled by a platinum resistance sensor connected to an external proportional temperature controller for controlling the temperature of the external band heaters.

In each hydroformylation reaction, about 15 milliliters (about 14 grams) of the rhodium catalytic precursor solution so prepared was charged to the autoclave reactor under nitrogen and heated to the reaction temperature employed (as given in Table 1 below). The reactor was then vented down to 5 psig. and 2.5 mL (about 1.5 grams) of butene-1 introduced into the reactor. Then carbon monoxide and hydrogen (partial pressures given in Table 1) were introduced into the reactor via the gas manifold and the trans-butene-1 so hydroformylated.

The hydroformylation reaction rate in gram moles per liter per hour of C5 aldehydes produced was determined from sequential 5 psia. pressure drops in the reactor spanning the nominal operating pressure in the reactor, while the mole ratio of linear (n-valeraldehyde) to branched (2-methylbutyraldehyde) product was measured by gas chromatography and the results are given in Table 1 below, said results being determined after about a 5 to 20 percent conversion of the butene-1 starting material.

TABLE 1

| Run No. | Ligand (Z=) | Solvent | Precursor Solution and Reaction Conditions | Ligand/ Rhodium Mole Ratio | Reaction Rate Gram Moles/ Liter/Hour | Linear/ Branched C5 Aldehyde Mole Ratio |
| --- | --- | --- | --- | --- | --- | --- |
| 1 | CH3 | (c) | (b) | 3.8 | 5.7 | 10.3 |
| 2 | C6H5 | (d) | (a) | 4.1 | 5.1 | 79.0 |

TABLE 1-continued

| Run No. | Ligand (Z=) | Solvent | Precursor Solution and Reaction Conditions | Ligand/ Rhodium Mole Ratio | Reaction Rate Gram Moles/ Liter/Hour | Linear/ Branched C$_5$ Aldehyde Mole Ratio |
|---|---|---|---|---|---|---|
| 3 | p-nonyl C$_6$H$_5$ | (e) | (a) | 3.3 | 5.2 | 74.4 |
| 4 | p-ClC$_6$H$_5$ | (d) | (a) | 4.0 | 9.7 | 78.4 |
| 5 | o-tolyl | (d) | (a) | 4.0 | 5.9 | 46.6 |

(a) = 250 ppm rhodium; 2 weight percent bis-phosphite ligand; 70° C.; 100 psia CO:H2 (1:2 mole ratio); 35 psia butene-1 (2.5 mL butene-1).

(b) = 330 ppm rhodium, 2 weight percent bis-phosphite ligand; 70° C. 50 psia CO:H$_2$ (1:4 mole ratio); 2.5 mL butene-1.

(c) = Toluene (d) = Valeraldehyde trimer (e) = Texanol*

EXAMPLE 2

The same procedure and conditions employed in Example 1 of preparing a series of rhodium catalytic precursor solutions using rhodium dicarbonyl acetylacetonate, a solvent and various bis-phosphite ligands having the formula:

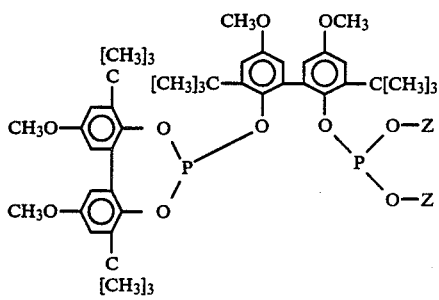

wherein each Z represents a radical as shown in TABLE 2 below and hydroformylating butene-1 were repeated, save for hydroformylating propylene instead of butene-1 and using a premixed gas composition of carbon monoxide, hydrogen and propylene after having adjusted the reaction pressure to 20 psia with nitrogen and varying the rhodium complex catalyst precursor solutions and hydroformylation reaction conditions as shown in said Table 2. The hydroformylation reaction rate in terms of gram moles per liter per hour of butyraldehyde produced as well as the mole ratio of linear (n-butyraldehyde) to branched (isobutyraldehyde) product were determined and the results are given in Table 2 below.

TABLE 2

| Run No. | Ligand (Z=) | Solvent | Precursor Solution and Reaction Conditions | Reaction Rate Gram Moles/ Liter/Hour | Linear/ Branched Butyraldehyde Mole Ratio |
|---|---|---|---|---|---|
| 1 | CH$_3$ | (c) | (a) | 1.33 | 3.14 |
| 2 | C$_6$H$_5$ | (d) | (b) | 1.86 | 29.4 |
| 3 | p-nonyl C$_6$H$_5$ | (d) | (b) | 2.26 | 23.8 |
| 4 | p-ClC$_6$H$_5$ | (d) | (b) | 1.96 | 27.0 |
| 5 | o-tolyl | (d) | (b) | 1.02 | 18.9 |

(a) = 330 ppm rhodium; 7.5 moles equivalents of bis-phosphite ligand per mole equivalents of rhodium; 85° C.; 75 psia CO:H2:Propylene (1:1:1 mole ratio)

(b) = 250 ppm rhodium, 4 moles equivalents of bis-phosphite ligand per mole equivalent of rhodium; 70° C.; psia CO:H$_2$Propylene (1:1:1 mole ratio)

(c) = Toluene (d) = Valeraldehyde trimer

EXAMPLE 3

The same procedure and conditions employed in Example 1 of preparing a rhodium catalytic precursor solution using rhodium dicarbonyl acetylacetonate, valeraldehyde trimer as solvent and a bis-phosphite ligand having the formula

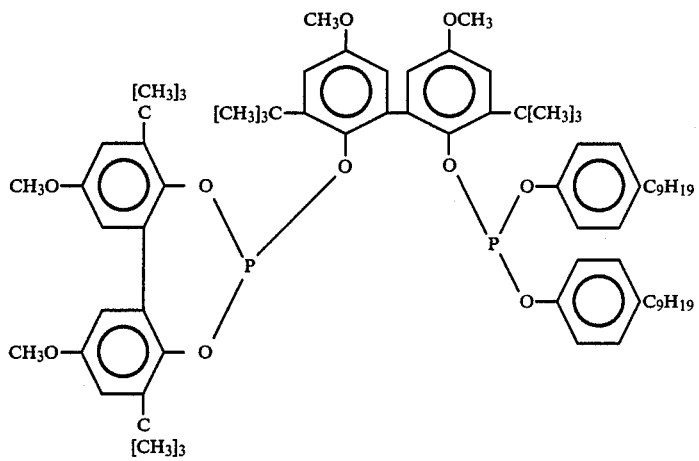

and hydroformylating butene-1 were repeated employing various different olefins as the starting hydroformylation material and varying the rhodium complex catalyst precursor solutions and hydroformylation reaction conditions as shown in Table 3 below. The hydroformylation reaction rate in terms of gram moles per liter per hour of aldehyde produced as well as the mole ratio of linear aldehyde to branched aldehyde product were determined as in Example 1 and the results are given in Table 3 below.

TABLE 3

| Olefin | (Rh) ppm | Ligand/Rh Mole Ratio | Partial Pressures | | | Temp. °C. | Reaction Rate Gram Moles/ Liter/Hour | Linear/ Branched Aldehyde Mole Ratio |
| | | | CO psia | H₂ psia | Olefin (mL) | | | |
| --- | --- | --- | --- | --- | --- | --- | --- | --- |
| Butene-1 | 125 | 4.0 | 33 | 67 | 2.5 | 70 | 3.05 | 68 |
| Butene-2 (trans) | 400 | 4.2 | 33 | 67 | 2.5 | 100 | 1.5 | 16 |
| Hexene-1 | 250 | 6.6 | 33 | 67 | 2.5 | 70 | 3.5 | 66 |
| Hexene-2 | 250 | 6.6 | 33 | 67 | 2.5 | 100 | 0.36 | 19 |
| Octene-1 | 250 | 6.6 | 33 | 67 | 2.5 | 70 | 2.1 | 93 |
| Octene-2 | 250 | 6.6 | 33 | 67 | 2.5 | 100 | 0.2 | 17 |
| Decene-1 | 250 | 6.6 | 33 | 67 | 2.5 | 70 | 1.2 | 80 |
| Decene-2 | 250 | 6.6 | 33 | 67 | 2.5 | 100 | 0.15 | 14 |

EXAMPLE 4

The same procedure and conditions employed in Example 1 of preparing a rhodium catalytic precursor solution using rhodium dicarbonyl acetylacetonate, valeraldehyde trimer as solvent and a bis-phosphite ligand having the formula

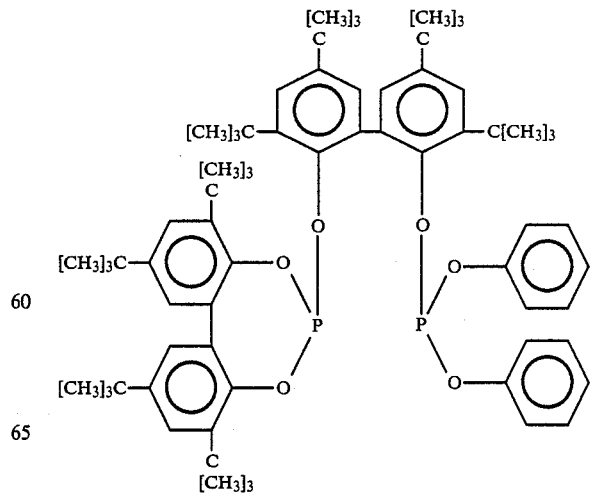

and hydroformylation butene-1 were repeated employing the rhodium complex catalyst precursor solution and hydroformylation reaction conditions shown in Table 4 below. The hydroformylation reaction rate in terms of gram moles per liter per hour of C5 aldehydes produced as well as the mole ratio of linear n-valeraldehyde to branched 2-methylbutyraldehyde product were determined as in Example 1 and the results are given in Table 4 below.

TABLE 4

| Reaction Rate Gram Moles/ Liter/Hour | Linear/ Branched C5 Aldehyde Mole Ratio |
|---|---|
| 5.7 | 39.7 |

Precursor Solution and Reaction Conditions: 250 ppm rhodium; 2 weight percent bis-phosphite ligand (7.7 mole equivalents of bis-phosphate ligand per mole equivalent of rhodium), 70° C., 100 psia CO:H2 (1:2 mole ratio); 35 psia butene-1.

EXAMPLE 5

The same procedure and conditions employed in Example 2 of preparing a rhodium catalytic precursor solution using rhodium dicarbonyl acetylacetonate, valeraldehyde trimer as solvent and a bis-phosphite ligand having the formula

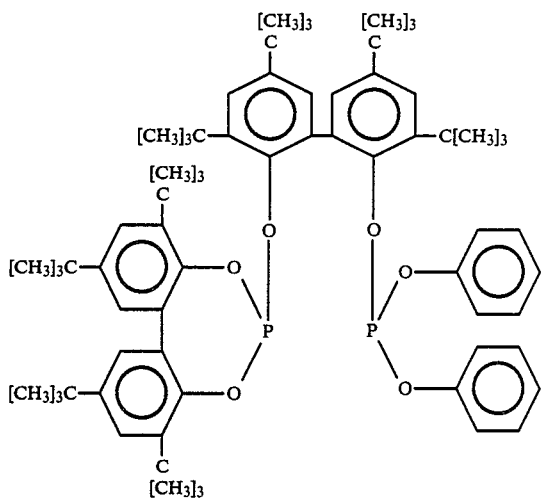

and hydroformylating propylene were repeated employing the rhodium complex catalyst precursor solution and hydroformylation reaction conditions as shown in Table 5 below. The hydroformylation reaction rate in terms of gram moles per liter per hour of butyraldehyde produced as well as the mole ratio of linear n-butyraldehyde to branched isobutyraldehyde product were determined and the results are given in Table 5 below.

TABLE 5

| Reaction Rate Gram Moles/ Liter/Hour | Linear/ Branched C5 Aldehyde Mole Ratio |
|---|---|
| 1.06 | 21.6 |

Precursor Solution and Reaction Conditions: 250 ppm rhodium; 4 mole equivalents of bisphosphite ligand per mole equivalent of rhodium, 70° C.; 90 psia CO:H2:Propylene (1:1:1 mole ratio).

EXAMPLE 6

The same procedure and conditions employed in Example 2 of preparing a rhodium catalytic precursor solution using rhodium dicarbonyl acetylacetonate, valeraldehyde trimer as solvent and a bis-phosphite ligand having the formula:

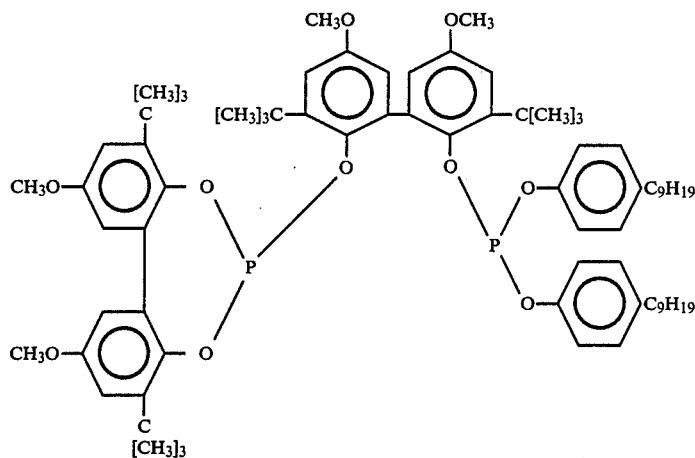

and hydroformylating propylene were repeated employing the rhodium complex catalyst precursor solutions and hydroformylation reaction conditions as shown in Table 6 below. The hydroformylation reaction rate in terms of gram moles per liter per hour of butyraldehyde produced as well as the mole ratio of linear (n-butyraldehyde) to branched (isobutyraldehyde) product were determined and the results are given in Table 6 below.

TABLE 6

| Run No. | Temp. °C. | Rh. ppm | Ligand/ Rhodium Mole Ratio | Partial Pressure | | | Reaction Rate Gram Moles/ Liter/Hour | Linear/Branched Butyraldehyde Mole Ratio |
|---|---|---|---|---|---|---|---|---|
| | | | | $H_2$ psia | CO psia | Propylene psia | | |
| 1 | 85 | 250 | 6.5 | 30 | 10 | 60 | 5.3 | 16.2 |
| 2 | 85 | 250 | 6.5 | 40 | 20 | 40 | 6.5 | 17.6 |
| 3 | 85 | 250 | 6.5 | 33.3 | 33.3 | 33.3 | 1.85 | 19.2 |
| 4 | 85 | 250 | 6.5 | 20 | 40 | 40 | 1.45 | 13.3 |
| 5 | 85 | 125 | 2.0 | 33.3 | 33.3 | 33.3 | 1.25 | 20.6 |
| 6 | 85 | 125 | 4.0 | 33.3 | 33.3 | 33.3 | 1.31 | 20.9 |
| 7 | 85 | 125 | 6.6 | 33.3 | 33.3 | 33.3 | 1.25 | 20.8 |
| 8 | 85 | 125 | 13.2 | 33.3 | 33.3 | 33.3 | 1.1 | 20.7 |
| 9 | 85 | 125 | 26.4 | 33.3 | 33.3 | 33.3 | 1.08 | 20.4 |
| 10 | 85 | 125 | 39.6 | 33.3 | 33.3 | 33.3 | 0.99 | 20.3 |
| 11 | 85 | 125 | 52.8 | 33.3 | 33.3 | 33.3 | 0.92 | 20.0 |
| 12 | 60 | 250 | 4.0 | 33.3 | 33.3 | 33.3 | 0.77 | 24.4 |
| 13 | 70 | 250 | 4.0 | 33.3 | 33.3 | 33.3 | 2.26 | 23.8 |
| 14 | 80 | 250 | 4.0 | 33.3 | 33.3 | 33.3 | 2.22 | 21.9 |
| 15 | 90 | 250 | 4.0 | 33.3 | 33.3 | 33.3 | 2.79 | 17.8 |
| 16 | 100 | 250 | 4.0 | 33.3 | 33.3 | 33.3 | 3.26 | 13.0 |

Runs Nos. 1 to 4 demonstrate the effect of varying carbon monoxide partial pressure on the process. Run Nos. 5 to 11 demonstrate the effect of varying bis-phosphite ligand concentration on the process. Run Nos. 12 to 16 demonstrate the effect of varying the reaction temperature of the process.

EXAMPLE 7

The same procedure and conditions employed in Example 1 of preparing a rhodium catalytic precursor solution using rhodium dicarbonyl acetylacetonate, a solvent and a bis-phosphite ligand and hydroformylating butene-1 were repeated using the various bis-phosphite ligands having the formula:

-continued

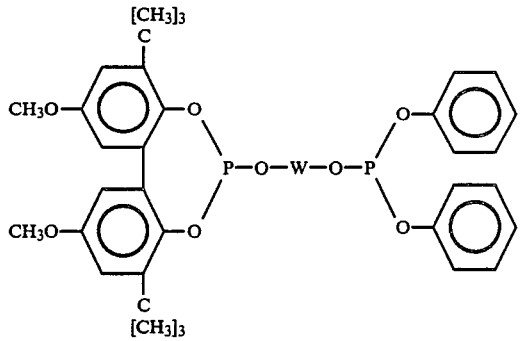

wherein W is a divalent bridging group as shown in TABLE 7 below, rhodium complex catalyst precursor solutions and hydroformylation reaction conditions as shown in said TABLE 7. The hydroformylation reaction rate in terms of gram moles per liter per hour of $C_5$ aldehydes (pentanals) produced as well as the mole ratio of linear (n-valeraldehyde) to branched (2-methylbutyraldehyde) product were determined in the same manner as in Example 1 and the results are given in Table 7 below.

TABLE 7

| Run No. | Ligand (W =) | Liquid/ Rh mole Ratio | Reaction Rate Gram Moles/ Liter/Hour | Linear/ Branched $C_5$ Aldehyde Mole Ratio |
|---|---|---|---|---|
| 1 | ⌬-⌬ | 8.2 | 5.08 | 79.0 |
| 2 | (naphthalene-like) | 9.2 | 3.22 | 13.3 |
| 3 | OMe / t-Bu substituted biphenyl | 8.2 | 0.99 | 6.9 |

Precursor Solution and Reaction Conditions: 250 ppm rhodium; 2 weight percent bis-phosphite ligand, 70° C.; 100 psia CO:$H_2$ (1:2 mole ratio); 2.5 mL butene-1 (35 psia butene-1). In Run No. 1 the solvent was Valeraldehyde trimer while in Run Nos. 2 and 3 the solvent was Texanol ® (2,2,4-trimethyl-1,3-pentanediol monoisobutyrate).

EXAMPLE 8

The same procedure and conditions employed in Example 2 of preparing a rhodium catalytic precursor solution using rhodium dicarbonyl acetylacetonate, a solvent and a bis-phosphite ligand and hydroformylating propylene were repeated using the various bis-phosphite ligands having the formula:

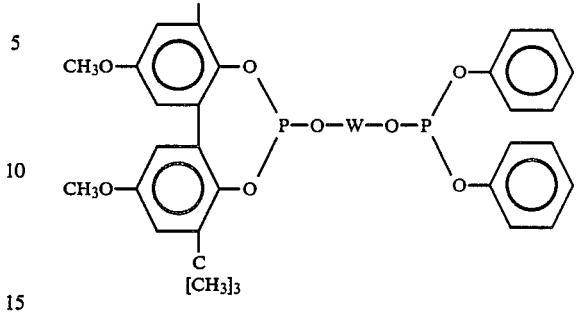

wherein W is a divalent bridging group as shown in TABLE 8 below, rhodium complex catalyst precursor solutions and hydroformylation reaction conditions as shown in TABLE 8 below. The hydroformylation reaction rate in terms of gram moles per liter per hour of butyraldehyde produced as well as the mole ratio of linear (n-butyraldehyde) to branched (isobutyraldehyde) product were determined and the results are given in TABLE 8 below.

TABLE 8

| Run No. | Ligand (W =) | Reaction Rate Gram Moles/ Liter/Hour | Linear/ Branched Butyraldehyde Mole Ratio |
|---|---|---|---|
| 1 | ⌬-⌬ | 1.86 | 29.4 |
| 2 | (naphthalene-like) | 0.50 | 5.7 |
| 3 | OMe / t-Bu substituted biphenyl | 0.20 | 2.3 |

Precursor solution and reaction conditions: 250 ppm rhodium; 4 mole equivalents of bis-phosphite ligand per mole equivalent of rhodium; 70° C.; 90 psia CO:$H_2$:propylene (1:1:1 mole ratio). In Run No. 1 the solvent was Valeraldehyde trimer while in Run Nos 2 and 3 the solvent was Texanol ®.

EXAMPLE 9

Continuous hydroformylation of butene-1 using a bis-phosphite ligand was conducted in the following manner.

The hydroformylation was conducted in a glass reactor operating in a continuous single pass butene-1 hydroformylation mode. The reactor consisted of a three-ounce pressure bottle submersed in an oil bath with a glass front for viewing. About 20-mL of a freshly prepared rhodium catalytic precursor solution was charged to the reactor with a syringe, after purging the system with nitrogen. The precursor solution contained about 250 ppm rhodium introduced as rhodium dicarbonyl acetylacetonate, about 2 weight percent of a bis-phosphite ligand of the formula

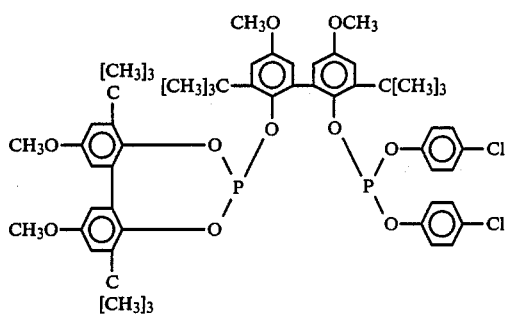

(about 8.0 equivalents of ligand per mole of rhodium) and Texanol ® as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-1 being given in Table 9 below, the remainder being nitrogen and aldehyde product. The flows of the feed gases (carbon monoxide, hydrogen, butene-1 and nitrogen) were controlled individually with mass flow meters and the feed gases dispersed into the precursor solution via fritted spargers. The reaction temperatures are given in TABLE 9 below. The unreacted portion of the feed gases was stripped out the product $C_5$ aldehydes and the outlet gas analyzed over about 5 days of continuous operation. The approximate daily average reaction rate, in terms of gram moles per liter per hour of product $C_5$ aldehydes, as well as the linear (n-valeraldehyde) to branched (2-methyl-butyraldehyde) product ratio are given in Table 9 below.

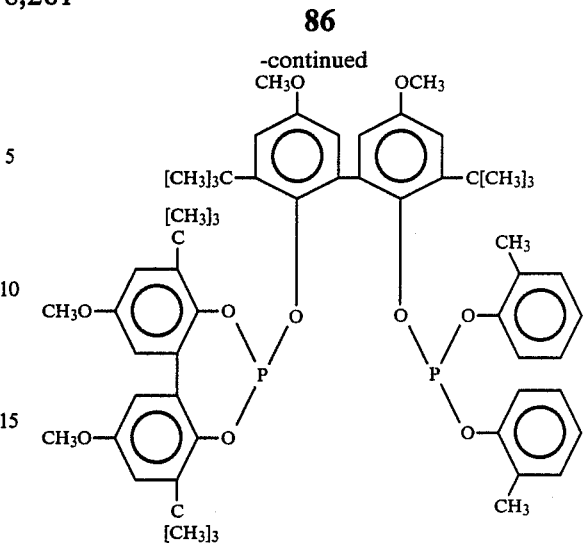

The hydroformylation was conducted in a glass reactor operating in a continuous single pass butene-1 hydroformylation mode. The reaction consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 250 ppm rhodium introduced as rhodium dicarbonyl acetylacetonate, about 2.0 weight percent of the bis-phosphite ligand (about 8.3 mole equivalents of the ligand per mole of rhodium) and Texanol ® as the solvent. After closing the reactor, the system was again purged with nitrogen and the oil bath was heated to furnish the desired hydroformylation reaction tempera-

TABLE 9

Test Results - Daily Averages

| Days Opern. | Temp. °C. | Rhodium ppm** | Ligand wt. % | Partial Pressures | | | Reaction Rate gram moles/ Liter/Hour | Linear/ Branched $C_5$ Aldehyde Mole Ratio |
| | | | | CO psia | $H_2$ psia | Butene-1 psia | | |
| --- | --- | --- | --- | --- | --- | --- | --- | --- |
| 1.0 | 71 | 250 | 2.0 | 30 | 62 | 2.0 | 0.86 | 68.0 |
| 1.9 | 71 | 154 | 1.2 | 26 | 66 | 3.0 | 1.33 | 54.4 |
| 3.0 | 71 | 163 | 1.3 | 25 | 63 | 2.0 | 1.64 | * |
| 4.0 | 71 | 156 | 1.2 | 25 | 62 | 2.0 | 1.59 | * |
| 5.0 | 72 | 180 | 1.4 | 25 | 63 | 2.0 | 1.58 | * |
| 5.4 | 72 | 201 | 1.6 | 25 | 63 | 2.0 | 1.94 | 76.9 |

*Stream not sampled for isomer ratio
**Changing values reflect change in daily liquid reactor solution levels.

EXAMPLE 10

Butene-1 was hydroformylated in the same manner as Example 9 using a bis-phosphite ligand having the formula ture. The hydroformylation reaction was conducted at a total gas pressure of bout 160 psig., the partial pressures of hydrogen, carbon monoxide, and butene-1 being given in Table 10 below, the remainder being nitrogen and aldehyde product. The flows of the feed gases (carbon monoxide, hydrogen and butene-1) were controlled individually with mass flow meters and the feed gases dispersed into the precursor solution via fritted spargers. The reaction temperatures given in TABLE 10 below. The unreacted portion of the feed gases was stripped out the product $C_5$ aldehydes and the outlet gas analyzed over about 5 days of continuous operation. The approximate daily average reaction rates in terms of gram moles per liter per hour of product C5 aldehydes as well as the linear n-valeraldehyde to 2-methylbutyraldehyde branched product ratio are given in Table 10 below.

mole of rhodium) and valeraldehyde trimer as the solvent. After closing the reactor, the system was again purged with nitrogen and the oil bath was heated to furnish the desired hydroformylation reaction temperature. The hydroformylation reaction was conducted at a total gas pressure of about 160 psig., the partial pres-

TABLE 10

Test Results - Daily Averages

| Days Opern. | Temp. °C. | Rhodium ppm** | Ligand wt. % | Partial Pressures | | | Reaction Rate gram moles/ Liter/Hour | Linear/ Branched C5 Aldehyde Mole Ratio |
| | | | | CO psia | H2 psia | Butene-1 psia | | |
|---|---|---|---|---|---|---|---|---|
| 1.0 | 71 | 250 | 2.0 | 32 | 60 | 4.0 | 1.04 | 20.0 |
| 1.9 | 71 | 178 | 1.4 | 27 | 62 | 4.0 | 1.60 | 20.0 |
| 2.9 | 71 | 176 | 1.4 | 27 | 64 | 3.0 | 1.52 | * |
| 3.9 | 71 | 176 | 1.4 | 26 | 66 | 3.0 | 1.70 | * |
| 5.0 | 72 | 179 | 4.4 | 25 | 67 | 3.0 | 1.80 | * |
| 5.4 | 72 | 182 | 1.5 | 25 | 66 | 4.0 | 1.81 | 26.4 |

*Stream not sampled for isomer ratio.
**Changing values reflect change in daily liquid reactor solution levels.

EXAMPLE 11

Butene-2 (about a 1:1 mole ratio of cis and trans butene-2) was hydroformylated in the same manner as Example 9 using a bis-phosphite ligand having the formula

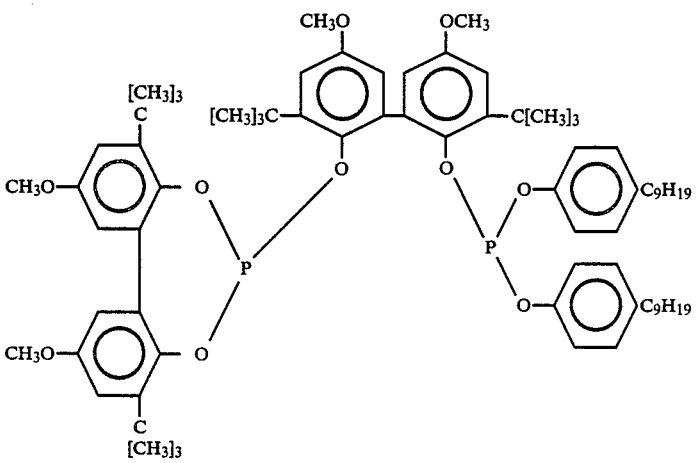

The hydroformylation was conducted in a glass reactor operating in a continuous single pass butene-2 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 125 ppm rhodium introduced as rhodium dicarbonyl acetylacetonate, about 7.0 weight of the bis-phosphite ligand (about 50 mole equivalents of the ligand per sures of hydrogen, carbon monoxide and butene-2 being given in TABLE 11 below, the remainder being nitrogen and aldehyde product. The flows of the feed gases (carbon monoxide, hydrogen and butene-2) were controlled individually with mass flow meters and the feed gases dispersed into the precursor solution via fritted spargers. The reaction temperatures given in TABLE 11 below. The unreacted portion of the feed gases was stripped out the product C5 aldehydes and the outlet gas analyzed over about 15 days of continuous operation. The approximate daily average reaction rates in terms of gram moles per liter per hour of product C5 aldehydes as well as the linear n-valeraldehyde to 2-methylbutyraldehyde branched product ratio are given in TABLE 11 below.

TABLE 11

Test Results - Daily Averages

| Days Opern. | Temp. °C. | Rhodium ppm** | Ligand wt. % | Partial Pressures | | | Reaction Rate gram moles/ Liter/Hour | Linear/ Branched C5 Aldehyde Mole Ratio |
| | | | | CO psia | H2 psia | Butene-2 psia | | |
|---|---|---|---|---|---|---|---|---|
| 1.0 | 95 | 125 | 7.0 | 20 | 60 | 14 | 0.44 | 4.31 |
| 1.9 | 95 | 112 | 6.3 | 19 | 55 | 36 | 1.03 | 24.39 |
| 2.9 | 95 | 112 | 6.3 | 18 | 56 | 38 | 1.25 | 29.66 |
| 4.0 | 94 | 112 | 6.3 | 17 | 54 | 45 | 1.34 | 35.15 |

TABLE 11-continued

Test Results - Daily Averages

| Days Opern. | Temp. °C. | Rhodium ppm** | Ligand wt. % | Partial Pressures | | | Reaction Rate gram moles/ Liter/Hour | Linear/ Branched C5 Aldehyde Mole Ratio |
| --- | --- | --- | --- | --- | --- | --- | --- | --- |
| | | | | CO psia | H2 psia | Butene-2 psia | | |
| 5.0 | 96 | 114 | 6.4 | 17 | 54 | 42 | 1.42 | 30.01 |
| 5.7 | 96 | 115 | 6.5 | 17 | 55 | 41 | 1.39 | 29.73 |
| 6.9 | 94 | 116 | 6.5 | 17 | 55 | 42 | 1.19 | 28.77 |
| 8.0 | 96 | 118 | 6.6 | 17 | 55 | 42 | 1.30 | 29.09 |
| 9.0 | 96 | 118 | 6.6 | 16 | 51 | 49 | 1.43 | 27.46 |
| 10.0 | 97 | 120 | 6.7 | 17 | 54 | 44 | 1.35 | 26.37 |
| 11.0 | 97 | 121 | 6.8 | 17 | 54 | 44 | 1.29 | 26.48 |
| 12.0 | 98 | 122 | 6.8 | 17 | 53 | 45 | 1.38 | 23.88 |
| 13.0 | 101 | 123 | 6.9 | 17 | 53 | 44 | 1.41 | 23.07 |
| 13.7 | 102 | 128 | 7.2 | 18 | 54 | 41 | 1.45 | 21.96 |
| 15.0 | 100 | 142 | 7.9 | 18 | 53 | 41 | 1.39 | 20.70 |
| 15.4 | 97 | 141 | 7.9 | 18 | 55 | 41 | 1.16 | 26.82 |

*Changing values reflect change in daily liquid reactor solution levels.

EXAMPLE 12

Butene-2 (about a 1:1 mole ratio of cis and trans-butene-2) was hydroformylate in the same manner as Example 9 using a bis-phosphite ligand having the formula

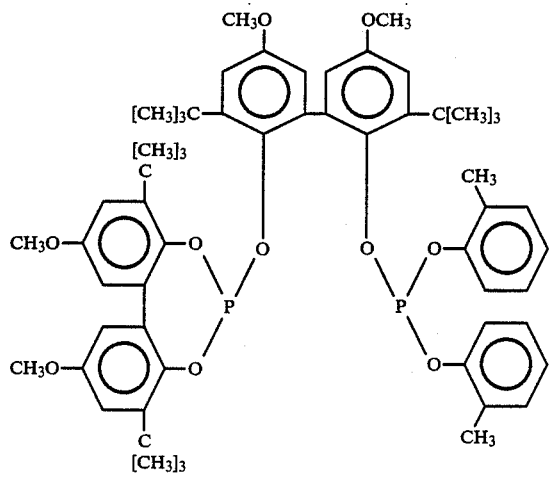

The hydroformylation was conducted in a glass reactor operating in a continuous single pass butene-2-hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 223 ppm rhodium introduced as rhodium dicarbonyl acetylacetonate, about 1.8 weight percent of the bis-phosphite ligand (about 8.3 mole equivalents of the ligand per mole of rhodium) and Texanol ® as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-2 being given in Table 12 below, the remainder being nitrogen and aldehyde product. The flows of the feed gases (carbon monoxide, hydrogen and butene-2) were controlled individually with mass flow meters and the feed gases dispersed into the precursor solution via fritted spargers. The reaction temperature given in TABLE 12 below. The unreacted portion of the feed gases was stripped out the product C5 aldehydes and the outlet gas analyzed over about 5.5 days of continuous operation. The approximate daily average reaction rates in terms of gram moles per liter per hour of product C5 aldehydes as well as the linear n-valeraldehyde to 2-methylbutyraldehyde branched product ratio are given in Table 12 below.

TABLE 12

Test Results - Daily Averages

| Days Opern. | Temp. °C. | Rhodium ppm* | Ligand wt. % | Partial Pressures | | | Reaction Rate gram moles/ Liter/Hour | Linear/ Branched C5 Aldehyde Mole Ratio |
| --- | --- | --- | --- | --- | --- | --- | --- | --- |
| | | | | CO psia | H2 psia | Butene-2 psia | | |
| 0.7 | 102 | 223 | 1.8 | 23 | 48 | 40 | 1.61 | 5.39 |
| 2.0 | 101 | 237 | 1.9 | 22 | 62 | 32 | 1.87 | 2.75 |
| 2.9 | 101 | 255 | 2.0 | 20 | 60 | 35 | 2.54 | 2.54 |
| 4.0 | 101 | 262 | 2.1 | 20 | 60 | 34 | 2.86 | 2.17 |
| 5.0 | 101 | 267 | 2.1 | 21 | 63 | 30 | 2.80 | 1.85 |
| 5.5 | 101 | 236 | 1.9 | 19 | 58 | 37 | 3.66 | 2.03 |

*Changing values reflect change in daily liquid reactor solution levels.

EXAMPLE 13

The bis-phosphite ligand having the formula:

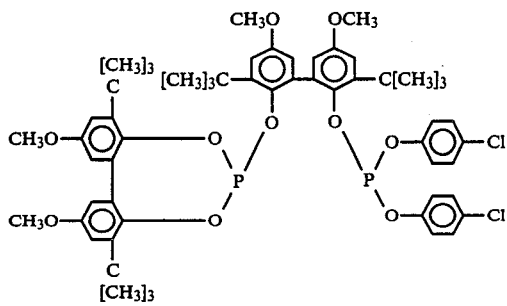

was prepared in the following manner:

About 179.2 grams (0.5 mole) of a 2,2'-dihydroxy-3,3'di-t-butyl-5,5'dimethoxy-1,1'-biphenyl diol was added to about 1600 mL of toluene. Sufficient toluene was then removed azetropically to remove residue traces of moisture. The dio-toluene solution was then allowed to cool to about 80° C. and about 168.7 grams (1.67 mole) of triethylamine added.

About 68.7 grams (0.5 mole) of phosphorus trichloride was added to about 200 mL of toluene and the diol-toluene-triethylamine solution then added to the PCl$_3$-toluene solution dropwise at −10° C. over about one hour and forty minutes. The reaction solution was held at this temperature for about 30 minutes and then allowed to warm to ambient temperature over a two hour period. The reaction medium was then filtered to remove the solid triethylamine-hydrochloride precipitate which was washed with two 200 mL portions of toluene. The combined filtrate and washes was then concentrated to give about a 717.5 gram solution of the phosphorochloridite intermediate:

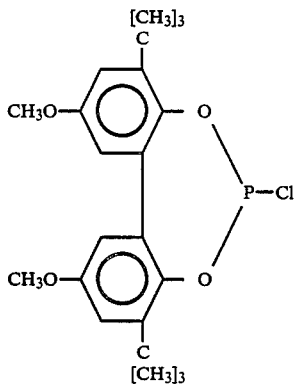

in toluene.

About 170.3 grams of additional 2,2'-dihydroxy-3,3'-di-t-butyl-5,5'-dimethoxy-1,1'-biphenyl diol was added to about 800 mL of toluene followed by about 48.1 grams of triethylamine. The above 717.5 grams of phosphorochloridite-toluene solution was then added dropwise over about 45 minutes at ambient temperature and the temperature increased to about 80° C. for one hour and 45 minutes followed by another temperature increase to about 95° C. for 2.0 hours and then allowed to cool to ambient temperature. About 600 mL of distilled water was then added to dissolve the solid triethylamine-hydrochloride precipitate and the solution allowed to settle and the two layers were then separated. The aqueous layer was then extracted with two 250 mL portions of toluene. The combined organic layer and extracts were then dried over anhydrous magnesium sulfate for one hour, filtered and concentrated to a residue product under vacuum. The residue product was then recrystallized from acetonitrile and about 242.5 grams (about 65.4 percent of theory) of the diorganophosphite intermediate,

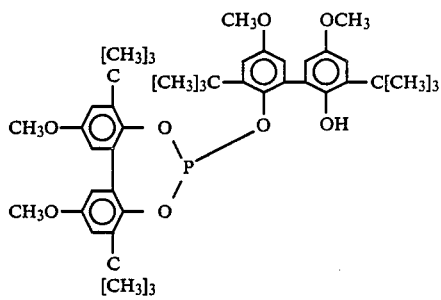

was recovered.

About 242.4 grams of the above recrystallized diorganophosphite intermediate was added to one liter of toluene followed by about 31.4 grams of triethylamine. About 42.7 grams of phosphorus trichloride was then added dropwise over about 5 minutes at ambient temperature and the temperature increased to reflux for about three hours and 45 minutes. The reaction solution was then cooled to about 68° C. and about 15.7 grams of triethylamine followed by about 21.3 grams of phosphorus trichloride was added. The reaction medium was then heated to relux for about 16 hours. The suspension was then cooled to about 20° C. and filtered to remove the solid triethylamine-hydrochloride precipitate which was washed with two 200 mL portions of toluene. The combine filtrate and washes was then concentrated under vacuum to give about a 516.2 gram solution of the phosphorodichloridite intermediate

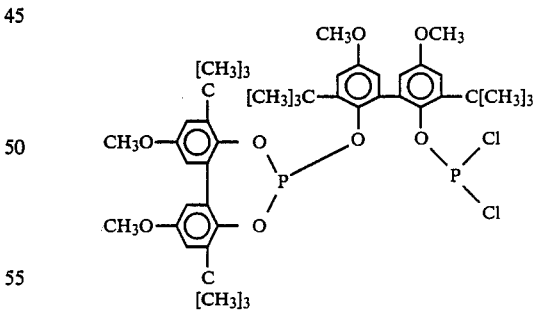

in toluene.

About 79.9 grams of para-chlorophenol was added to about 500 mL of toluene followed by about 62.9 grams of triethylamine. The above 516.2 grams of phosphorodichloridite-toluene solution was then added dropwise over one hour and 55 minutes at ambient temperature. The reaction solution was allowed to stir at ambient temperature for an additional two hours and 15 minutes. About 600 mL of distilled water was then added to dissolve the solid triethylamine-hydrochloride precipitate and the solution allowed to settle, and the two layers were then separated. The aqueous layer was then extracted with two 250 mL portions of toluene. The combined organic layer and extracts were then dried over magnesium sulfate, filtered and concentrated to a residue product under vacuum. The residue product was then recrystallized from acetonitrile and about 200 grams (about 62.5 percent of theory) of the desired bis-phosphite ligand product having the above formula was recovered and is designated herein as Ligand 1.

In the same manner the following bisphosphite ligands (Ligands 2 to 8) were prepared employing the appropriate diphenolic and mono-ol compounds that correspond to and account for their structures.

Ligand 2

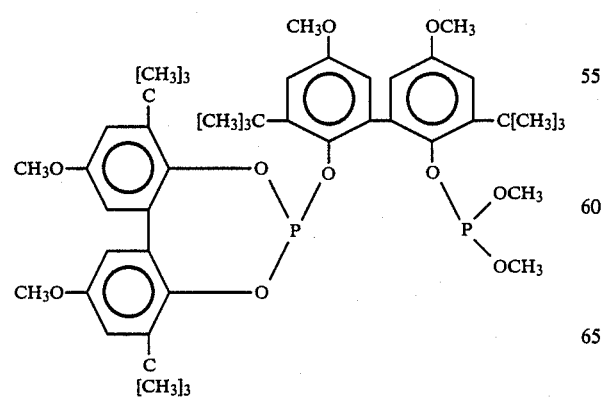

Ligand 3

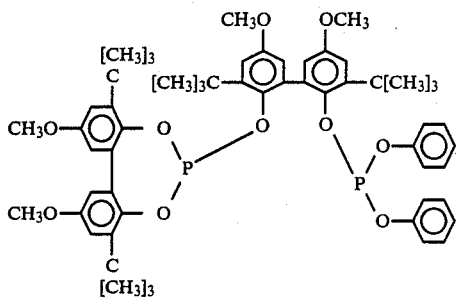

Ligand 4

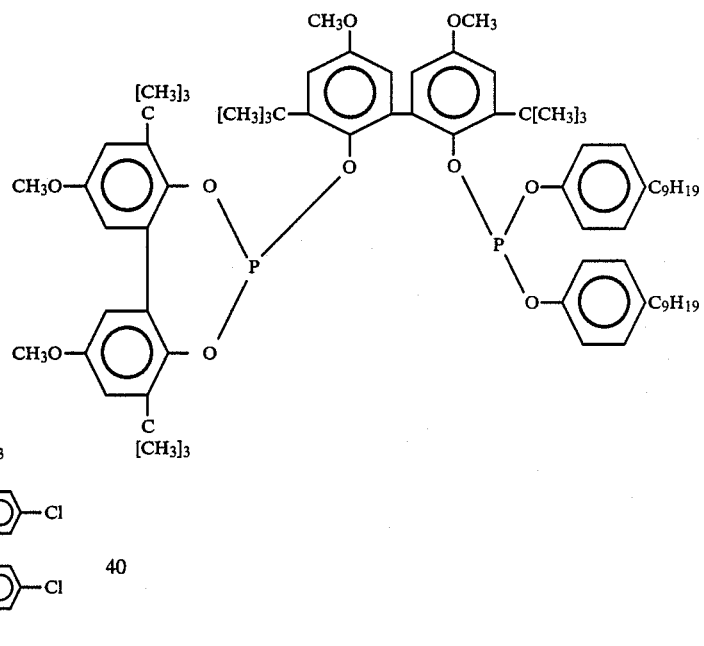

Ligand 5

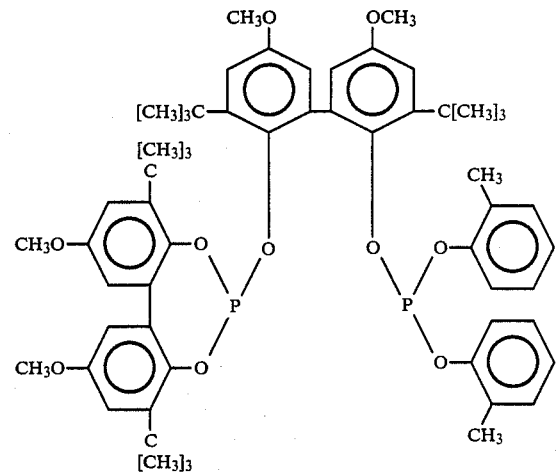

Ligand 6

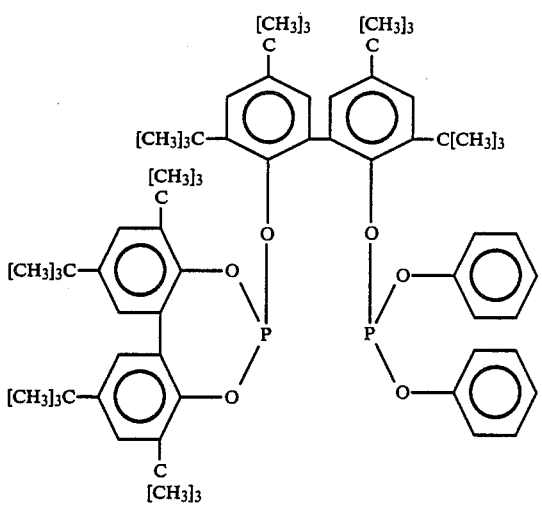

Ligand 7

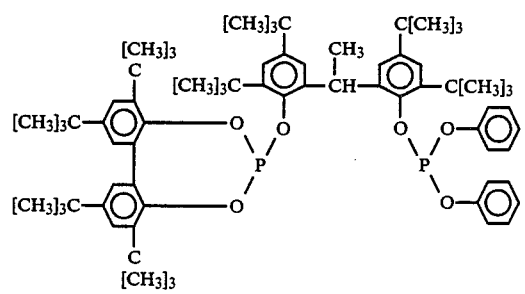

Ligand 8

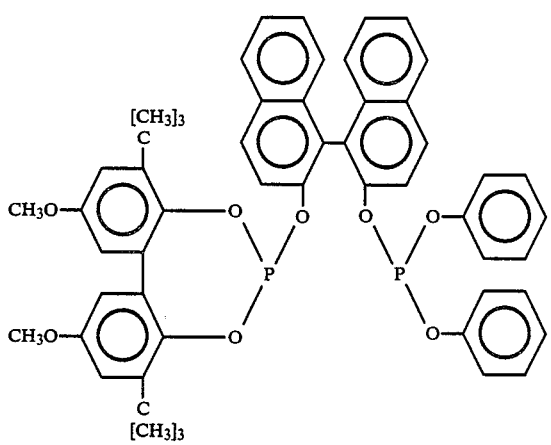

The structures of the above bis-phosphite ligands were confirmed by using Phosphorus-31 Nuclear Magnetic Resonance Spectroscopy (P-31 NMR) and Fast Atom Bombardment Mass Spectroscopy (FABMS). The bis-phosphite ligands may be identified by their characteristic P-31 NMR spectrum [i.e., pairs of doublets showing a phosphorus-phosphorus coupling constant (Jp1-p2 (Hz)] and by FABMS to show a mass corresponding to the mass of the molecular ion of the particular bis-phosphite as seen e.g. by the following analyticaly data.

| | Phosphorus-31 NMR Data | | | FAB Mass Spectra |
| | P-31 Chemical Shifts (ppm relative to phosphoric acid) | | | Mass of Molecular |
| Ligand | P1 | P2 | Jp1-p2 (Hz) | Ion |
|---|---|---|---|---|
| 1 | 140.1 | 137.3 | 6.6 | 1029 (MH+) |
| 2 | 140.6 | 137.6 | 5.3 | 836 (M+) |
| 3 | 140.3 | 137.7 | 6.7 | — |
| 4 | 139.9 | 137.1 | 19.1 | 1213 (M+) |
| 5 | 140.4 | 139.8 | 4.6 | 989 (M+) |
| 6 | 140.3 | 137.1 | 4.8 | 1065 (M+) |
| 7 | 139.1 | 133.8 | 72.3 | — |
| 8 | 137.3 | 127.7 | — | — |

EXAMPLE 14

A rhodium complex of the bis-phosphite ligand (said ligand being Ligand 3 of Example 13 above was prepared in the following manner.

To a solution of 0.5 grams (0.5 m moles) of said ligand in 10 mL. of dichloromethane were added 0.1 grams (0.25 m moles) of chlorodicarbonyl rhodium dimer [RhCl(CO)$_2$]$_2$. The mixture was stirred at ambient temperature for four and one-half hours to complete the reaction, as evidenced by the cessation of evolution of carbon monoxide. The reaction solution was then concentrated to a residue product under vacuum, and recrystallized from hexane yielding 0.14 grams of a crystalline solid which was unambiguously characterized as the cis-chelate chlorocarbonyl rhodium complex of said ligand having the formula

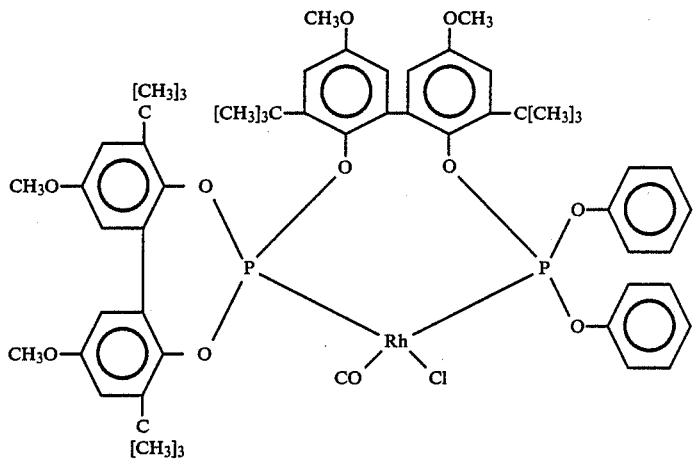

by X-ray crystallographic analysis. Said complex product's phosphorus-31 NMR spectrum in solution also corresponded to that of a cis-chelate rhodium complex.

Said rhodium-chloride-bis-phosphite complex (referred to as Complex A in Table 14 below) was employed to hydroformylate propylene in the same manner as outlined in Example 2 above and was found to exhibit very good hydroformylation activity despite the presence of the rhodium bound chloride, under the reaction conditions outlined in Table 14. Said rhodium-chloride-bis-phosphite complex catalyst was also compared to a rhodium-bis-phosphite ligand complex catalyst containing the same ligand, but free from chloride, its precursor being rhodium dicarbonyl acetylacetonate instead of [RhCl(CO)$_2$]$_2$. This chloride-free rhodium-ligand complex is referred to as Complex B in Table 14 below. The hydroformylation reaction rate in terms of gram moles per liter per hour of butyraldehyde produced as well as the mole ratio of linear n-butylraldehyde to branched isobutyraldehyde product of the experiments conducted are also given in Table 14.

TABLE 14

| Test No. | Catalyst Composition | Temp. °C. | Reaction Rate | N/I Ratio |
|---|---|---|---|---|
| 1 | Complex A | 80 | 0.38 | 6.5 |
| 2. | Complex A + 1 wt. % free ligand | 80 | 0.58 | 12.4 |
| 3. | Complex A | 100 | 0.45 | 3.7 |
| 4. | Complex A + 1 wt. % free ligand | 100 | 1.2 | 7.3 |
| 5. | Complex B + 2 wt. % free ligand | 80 | 2.2 | 22.8 |
| 6. | Complex B + 1 mole equivalent of allyl chloride | 80 | 0.45 | 21.3 |
| 7. | Complex B + 2 wt. % free ligand | 100 | 6.86 | 17.6 |
| 8. | Complex B + 1 mole equivalent allyl chloride | 100 | 1.12 | 12.2 |

Conditions: 250 ppm rhodium; 100 psia H$_2$:CO:Propylene (1:1:1 mole ratio)

While the rhodium catalyst of Complex A did exhibit good activity, its rhodium bound chloride appears to have a negative effect on obtaining high linear to branched aldehyde product ratios and thus should be preferably avoided when such high normal to isomer branched aldehyde products are desired.

Various modifications and variations of this invention will be obvious to a worker skilled in the art and it is to be understood that such modifications and variations are to be included within the purview of this application and the spirit and scope of the appended claims.

What is claimed is:

1. A bis-phosphite ligand selected from the class consisting of the formulas

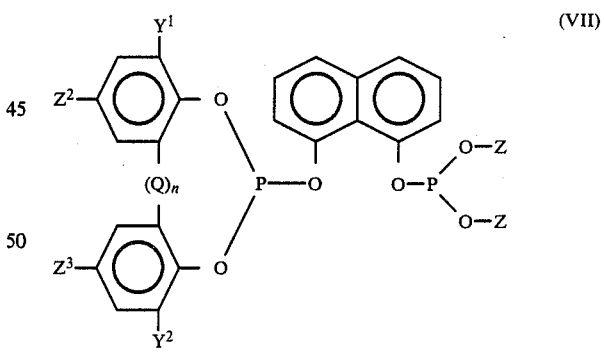

(VII)

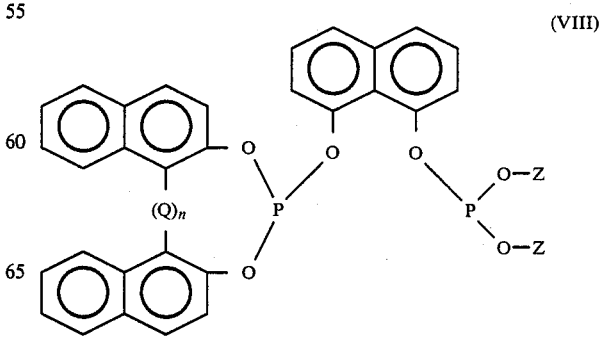

(VIII)

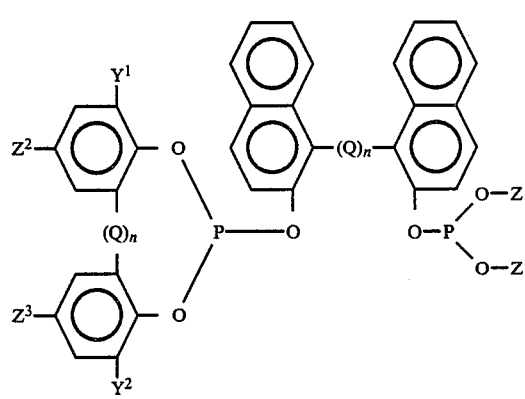
(IX)

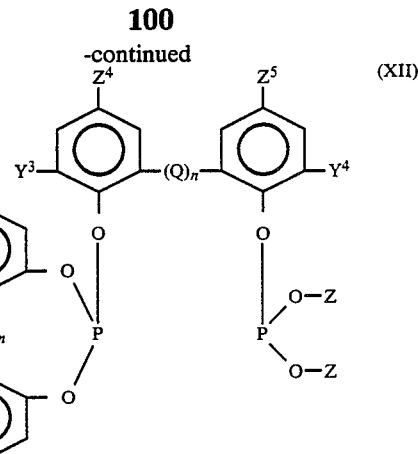
(XII)

wherein in Formulas VII, VIII, IX, X, XI, and XII, Q is —$CR^1R^2$ wherein each $R^1$ and $R^2$ radical individually represents a radical selected from the group consisting of hydrogen, alkyl of 1 to 12 carbon atoms, phenyl, tolyl and anisyl; wherein each $Y^1$, $Y^2$, $Y^3$, $Y^4$, $Z^2$, $Z^3$, $Z^4$ and $Z^5$ group individually represents a radical selected from the group consisting of hydrogen, an alkyl radical having from 1 to 18 carbon atoms, phenyl, benzyl, cyclohexyl, 1-methylcyclohexyl, cyano, halogen, nitro, trifluoromethyl, hydroxy, carbonyloxy, amino, acyl, phosphonyl, oxycarbonyl, amido sulfinyl, sulfonyl, silyl, alkoxy and thionyl radicals; wherein each Z group individually represents an identical or different radical selected from the group consisting of unsubstituted monovalent hydrocarbon alkyl, aryl, aralkyl, alkaryl and alicyclic radicals and a substituted phenyl radical containing a substituent radical selected from the group consisting of unsubstituted monovalent hydrocarbon alkyl, aralkyl, alkaryl and alicyclic radicals, as well as cyano, halogen, nitro, trifluoromethyl, hydroxy, amino, acyl, carbonyloxy, oxycarbonyl, amido, sulfonyl, sulfinyl, silyl, alkoxy, phosphonyl and thionyl radicals; and wherein n has a value of 0 or 1.

2. A bis-phosphite as defined in claim 1, wherein $Y^1$, $Y^2$, $Y^3$, and $Y^4$ are branched chain alkyl radicals having three to five carbon atoms, wherein $Z^2$, $Z^3$, $Z^4$, and $Z^5$ are hydrogen, an alkyl radical, a hydroxy radical or an alkoxy radical, and wherein each Z group is an aryl radical of the formula

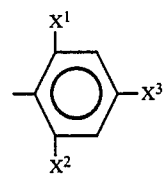

wherein each $X^1$, $X^2$, and $X^3$ radical individually represents a radical selected from the group consisting of hydrogen, an alkyl radical having from 1 to 18 carbon atoms, phenyl, benzyl, cyclohexyl, 1-methylcyclohexyl, cyano, halogen, nitro, trifluoromethyl, hydroxy, amino, acyl, carbonyloxy, oxycarbonyl, amido, sulfonyl, sulfinyl, silyl, alkoxy, phosphonyl, and thionyl radicals, and wherein Q, and n are the same as defined above.

3. A bis-phosphite as defined in claim 2, wherein the ligand is a ligand of Formula XI and wherein $Y^1$, $Y^2$, $Y^3$ and $Y^4$ each represent a tertiary butyl radical, wherein each $Z^2$, $Z^3$, $Z^4$ and $Z^5$ radical represents a methoxy radical and n is zero.

4. A bis-phosphite ligand as defined in claim 3, wherein $X^1$ and $X^3$ are hydrogen and $X^2$ is a methyl radical.

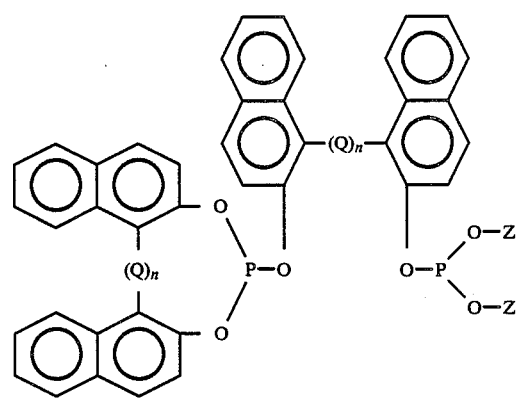
(X)

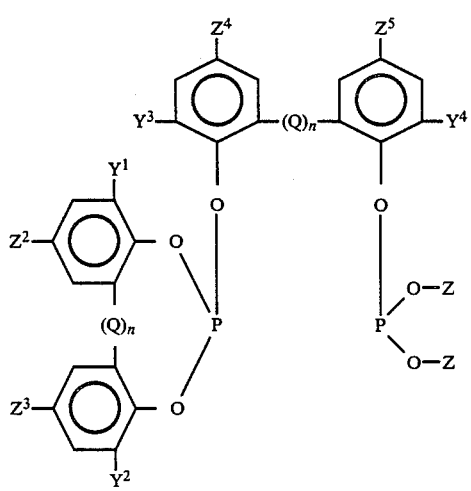
(XI)

and

* * * * *